United States Patent
Hayashi et al.

(10) Patent No.: US 10,829,512 B2
(45) Date of Patent: Nov. 10, 2020

(54) SELECTIVE DISULFIDATION REAGENT USING NITROGEN-CONTAINING COMPOUND AND METHOD FOR PRODUCING DISULFIDE-CONTAINING COMPOUND

(71) Applicants: Tokyo University of Pharmacy & Life Sciences, Tokyo (JP); Kokusan Chemical Co., Ltd., Tokyo (JP)

(72) Inventors: Yoshio Hayashi, Tokyo (JP); Akihiro Taguchi, Tokyo (JP); Kentaro Fukumoto, Tokyo (JP)

(73) Assignees: Tokyo University of Pharmacy & Life Sciences, Tokyo (JP); Kokusan Chemical Co., Ltd., Tokyo (JP)

(*) Notice: Subject to any disclaimer, the term of this patent is extended or adjusted under 35 U.S.C. 154(b) by 0 days.

(21) Appl. No.: 16/303,008

(22) PCT Filed: May 22, 2017

(86) PCT No.: PCT/JP2017/019086
§ 371 (c)(1),
(2) Date: Nov. 19, 2018

(87) PCT Pub. No.: WO2017/200109
PCT Pub. Date: Nov. 23, 2017

(65) Prior Publication Data
US 2019/0169228 A1    Jun. 6, 2019

(30) Foreign Application Priority Data
May 20, 2016  (JP) .................................. 2016-101812

(51) Int. Cl.
| | | |
|---|---|---|
| C07D 213/02 | (2006.01) | |
| C07D 471/04 | (2006.01) | |
| C07D 401/12 | (2006.01) | |
| C07K 1/08 | (2006.01) | |
| C07K 1/02 | (2006.01) | |
| C07D 213/80 | (2006.01) | |
| C07K 1/06 | (2006.01) | |

(52) U.S. Cl.
CPC ............ *C07K 1/086* (2013.01); *C07D 213/80* (2013.01); *C07D 401/12* (2013.01); *C07K 1/02* (2013.01); *C07D 471/04* (2013.01); *C07K 1/061* (2013.01)

(58) Field of Classification Search
CPC .................................................. C07D 213/02
USPC ........................................................ 546/255
See application file for complete search history.

(56) References Cited

U.S. PATENT DOCUMENTS

2016/0304459 A1   10/2016   Hayashi et al.

FOREIGN PATENT DOCUMENTS

| JP | 54-128578 | 10/1979 |
|---|---|---|
| JP | 54128578 | * 10/1979 |
| JP | 06-080691 | 3/1994 |
| WO | 2015050199 A2 | 4/2015 |

OTHER PUBLICATIONS

Taguchi et al., Chemistry—A European Journal (2017), 23(34), 8262-8267.*
Duthaler et al., European Journal of Organic Chemistry (2011), 2011(36), 7419.*
Duthaler et al., European Journal of Organic Chemistry (2011), 2011(24), 4667-4680, S4667/1-S4667/45.*
Matsueda et al., Heterocycles (1981), 15(2), 1089-92.*
Matsueda et al., Chemistry Letters (1978), (9), 951-2.*
Fujii, et al: "New Procedure for the Synthesis of Cystine-Peptides by Oxidation of S-Substituted Cysteine-Peptides with Thallium(iii) Trifluoracetate", J. Chem. Soc., Chem. Commun., 1987, pp. 163-164.
Fujii, et al: "Sulphoxide-Directed Disulphide Bond-Forming Reaction for the Synthesis of Cystine Peptides", J. Chem. Soc., Chem. Commun., 1987, pp. 1676-1678.
Akaji, et al: "Synthesis of Cystine-Peptide by a New Disulphide Bond-Forming Reaction Using the Silyl Chloride-Sulphoxide System", J. Chem. Soc., Chem. Commun., 1991, pp. 167-168.
Matsueda, et al: "Activation of Convention S-Protecting Groups of Cysteine by Conversion into the 3-Nitro-2-Pyridinesulfenyl (NPYS) Group", Chemistry Letters, 1982, pp. 921-924.
Taguchi et al: "3-Nitro-2-Pyridinesulfenates as Efficient Solution- and Solid-Phase Disulfide Bond Forming Agents", Chem. Euir. J. 2017, vol. 23, pp. 8262-8267.
Rosen et al: "Thiolysis of the 3-Nitro-2-Pyridinesulfenyl (Nyps) Protecting Group", Int. J. Peptide Protein Res., vol. 35, 1990, pp. 545-549.

(Continued)

*Primary Examiner* — Niloofar Rahmani
(74) *Attorney, Agent, or Firm* — Fox Rothschild LLP

(57) ABSTRACT

The present invention provides a means capable of selectively introducing a disulfide bond with respect to two free thiol groups located in a molecule of an organic compound such as a peptide, or the like, in a short time by a simple treatment and also by a chemically stable method.

A nitrogen-containing compound represented by Chemical Formula 1 below or a salt thereof:

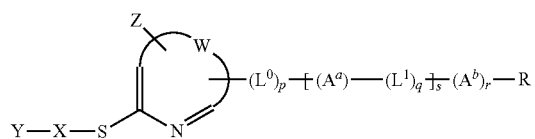

The symbols shown in Chemical Formula 1 are the same as defined in the specification.

27 Claims, 9 Drawing Sheets

Specification includes a Sequence Listing.

(56) References Cited

OTHER PUBLICATIONS

Matsueda, et al: "3-Nitro-2-Pyridinesulfenyl (NPYS) Group, A Novel Selective Protecting Group Which Can Be Activated for Peptide Bond Formation", Int. J. Peptide Protein Res., vol. 16, 1980, pp. 392-401.
Matsueda et al: "Synthesis of 3-Nitro-2-Pyridinesulferates", Meterocycles, vol. 15, No. 2, 1981, pp. 1089-1092.
Olsen, et al: "Npys-Mediated Elimination Reactions of Alcohols and Thiols: A Facile Route to Dehydroalanine and Dehydrobutyrine Building Blocks", Synlett, 2015, vol. 26, pp. 2697-2701.
Matsueda et al: "3-Nitro-2-Pyridinesulfenyl Protecting Group: Activatable Protecting Group for Peptide Synthesis and Enzyme Modification", Peptide Chemistry 1980, Proceedings of the 18th Symposium on Peptide Chemistry, Nishinomiya, Nov. 15-16, 1980, pp. 31-36.
International Search Report and Written Opinion dated Nov. 23, 2017 for PCT International Application No. PCT/JP2017/019086.

\* cited by examiner

FIG. 1
A) Before addition of 2a
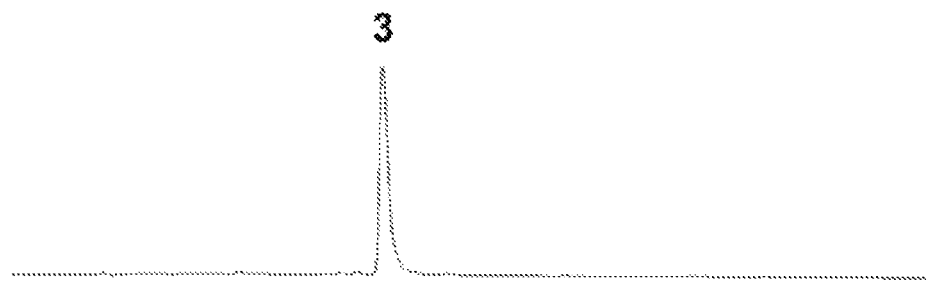
B) 1 h
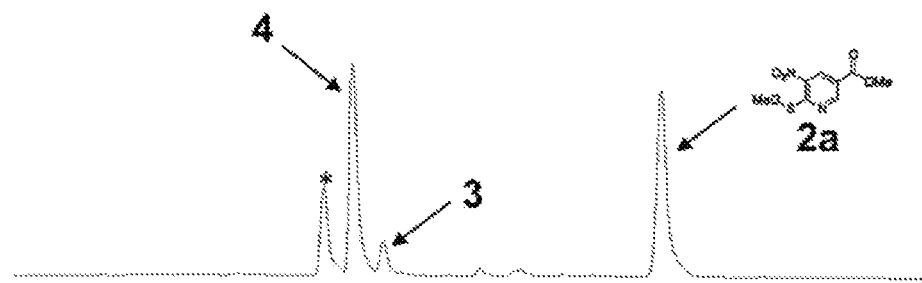
C) 6 h
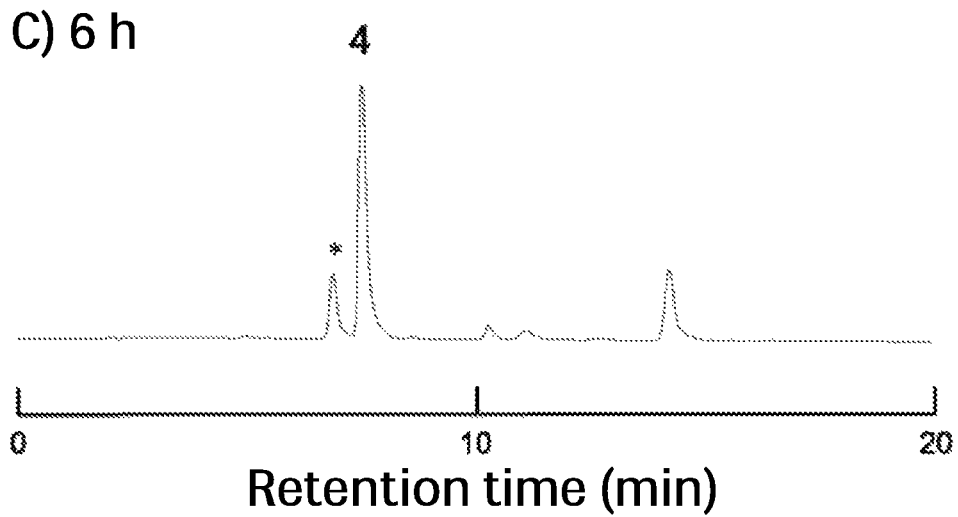
Retention time (min)

FIG. 2
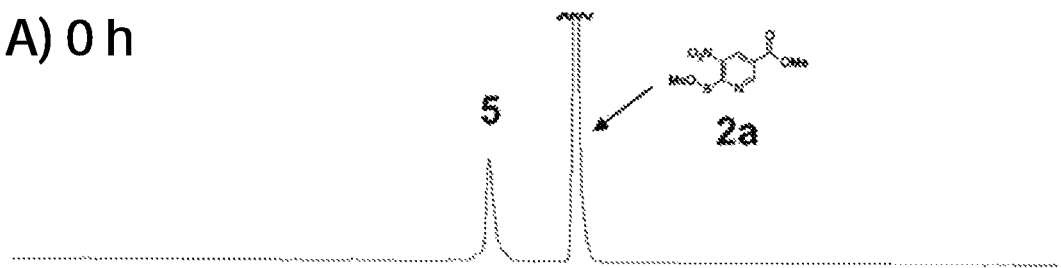
A) 0 h
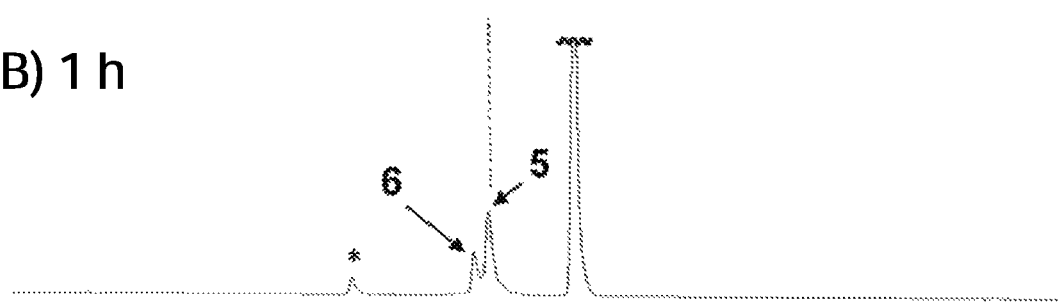
B) 1 h
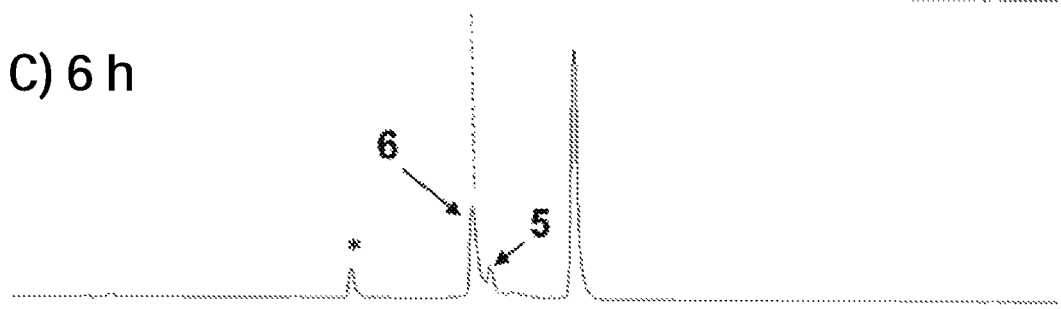
C) 6 h
D) 24 h
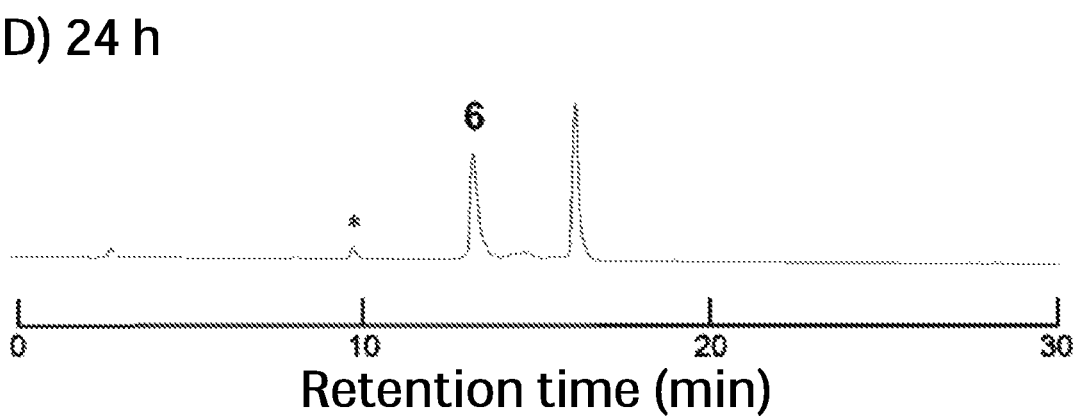
Retention time (min)

FIG. 3
A) 0 h
B) 4 h
C) 9 h
D) 27 h
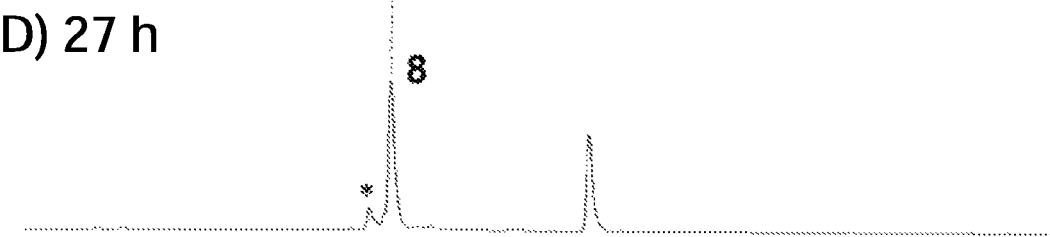
E) After HPLC purification
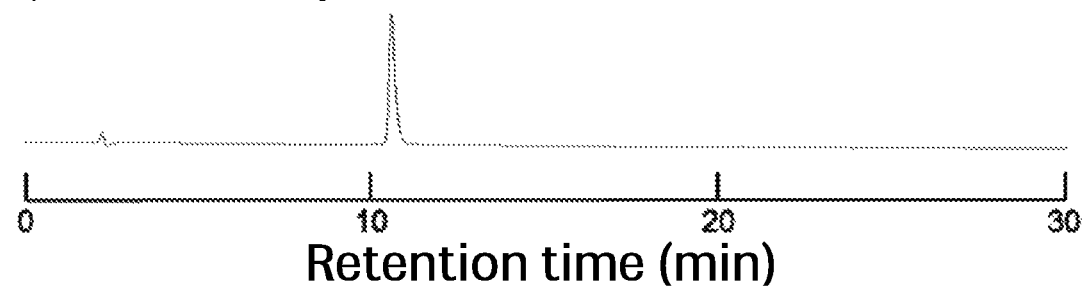
Retention time (min)

FIG. 4
A) Before addition of I2
B) 0 h (2 min)
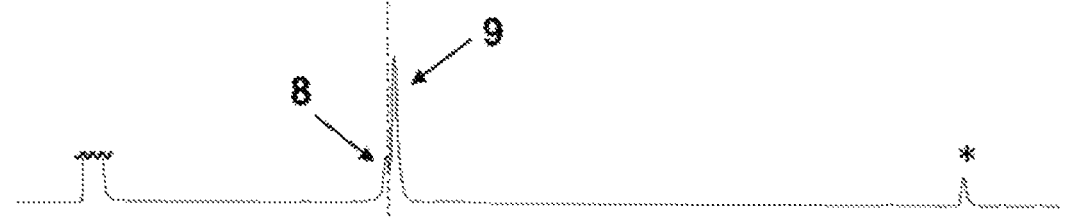
C) 1 h
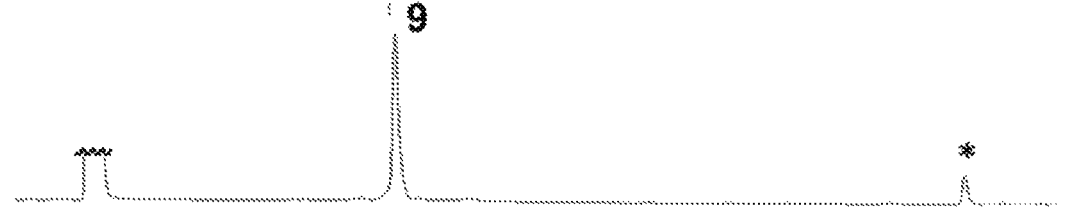
D) After purification
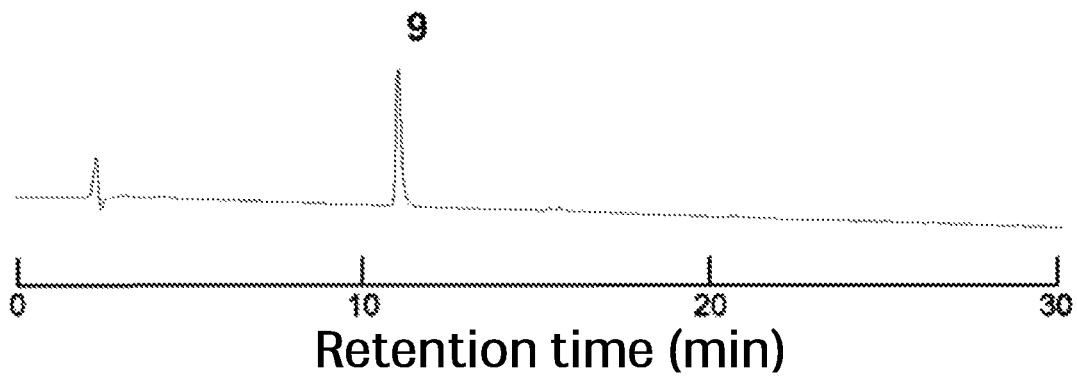
Retention time (min)

FIG. 5

A) Synthesized α-conotoxin Iml
10.773 min

B) Commercially available α-conotoxin Iml
10.78 min

C) Simultaneous injection
10.787 min

Retention time (min)

SELECTIVE DISULFIDATION REAGENT USING NITROGEN-CONTAINING COMPOUND AND METHOD FOR PRODUCING DISULFIDE-CONTAINING COMPOUND

TECHNICAL FIELD

The present invention relates to a pyridine derivative which is usable as a selective disulfidation reagent for a thiol group (—SH group) contained in an amino acid, a peptide, or the like, in organic synthesis (in particular, peptide synthesis, or the like). In addition, the present invention relates to a method for producing a disulfide-containing compound using the disulfidation reagent.

BACKGROUND ART

Conventionally, as a method for synthesizing a disulfide bond (S—S bond)-containing peptide, there is a known method for synthesizing a protective peptide sequence including a protected cysteine (Cys) residue by a solid phase method or a liquid phase method, deprotecting the entire protecting group to obtain a peptide having a free thiol group, and forming a disulfide bond (S—S bond) in a molecule using an air oxidation method or an iodine oxidation method.

However, the air oxidation method has a problem in that a long time is required to form a disulfide bond. In addition, the iodine oxidation method is known to cause iodine oxidation to tyrosine, histidine, and tryptophan during a reaction, and has a problem in that selectivity is not sufficient. In addition, when the disulfide bond is formed in a molecule by using these methods, if the concentration of the free thiol group-containing peptide in the reaction system is excessively high, the disulfide bond is formed between molecules to form a crosslinking isomer, thus causing problems in that the yield of the desired disulfide-containing peptide is lowered, and an operation for separating and purifying the desired peptide from the crosslinking isomer is required, and further, generally, performing a reaction under high dilution is required.

In addition, as a method for chemically forming a disulfide bond, a thallium (III) trifluoroacetate method (see Non-Patent Literature 1), a S-protected cysteine sulfoxide method (see Non-Patent Literature 2), and a silylchloride sulfoxide method (see Non-Patent Literature 3) have been reported as reactions to form the disulfide bond simultaneously with deprotection. Further, it has also been reported that an intermolecular disulfide bond can be easily formed by using and reacting a 3-nitro-2-pyridinsulfenyl group (Npys group), as a protecting group of a thiol group of cysteine, with a free thiol group (See Non-Patent Literature 4).

Furthermore, Patent Literature 1 suggests a method for producing a disulfide-containing peptide by reacting cysteine or a cysteine-containing protected peptide, in which a thiol group is protected with an Npys group, with cysteine or a cysteine-containing protected peptide having a free thiol group, thereby sequentially performing a formation reaction of a disulfide bond and a formation reaction of a peptide bond.

CITATION LIST

Patent Literatures

Patent Literature 1: JP 6-80691 A

Non-Patent Literatures

Non-Patent Literature 1: J. Chem. Soc., Chem. Commun., 1987, 163-164
Non-Patent Literature 2: J. Chem. Soc., Chem. Commun. 1987, 1676-1678
Non-Patent Literature 3: J. Chem. Soc., Chem. Commun., 1991, 167-168
Non-Patent Literature 4: Chemistry Letters, 1982, 921-924

SUMMARY OF INVENTION

Technical Problem

However, since 3-nitro-2-pyridinesulfenyl chloride (Npys-Cl), which is a reagent used for introduction of an Npys group for protecting a thiol group described in Patent Literature 1, is a chemically unstable compound due to abundant reactivity thereof, there are problems in that the reagent reacts not only with the thiol group but also with various functional groups (amino group, hydroxyl group, etc.). Here, a document (Heterocycles, Vol. 15, No. 2, 1981) describes in regard to 3-nitro-2-pyridinesulfenyl halides that "They have been found to be extraordinarily stable solids that can be safely stored at least one year in a refrigerator". However, in fact, the above compound cannot be stored at room temperature due to high reactivity thereof. In addition, the compound is decomposed by moisture (water) during preservation, or unstable in a solution containing an alcohol, an amine, or the like, or even in a slightly basic solution, and thus it is practically not easy to preserve the compound. Further, the method described in Patent Literature 1 is based on the premise that the formation of disulfide bond and the formation of peptide bond are performed in stages after first synthesizing two types of protected peptide sequences, and then deprotection treatment is further performed. For this reason, there is also a problem in that the operation is complicated, for example, a process of protection and deprotection is required.

Therefore, an object of the present invention is to provide a means capable of selectively introducing a disulfide bond with respect to two free thiol groups located in a molecule of an organic compound such as a peptide, or the like, in a relatively short time by a simple treatment and also by a chemically stable method.

Solution to Problem

The present inventors conducted intensive studies to solve the above-described problems. They surprisingly found that the above problem was able to be solved by using a nitrogen-containing compound having a predetermined chemical structure as a disulfidation reagent, and completed the present invention. In addition, most of the nitrogen-containing compounds having the predetermined chemical structure are novel compounds.

In other words, according to an aspect of the present invention, there is provided a compound represented by Chemical Formula 1 below or a salt thereof, as a novel nitrogen-containing compound:

[Chemical Formula 1]

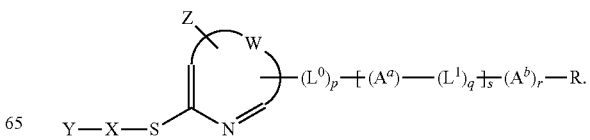

In Chemical Formula 1,

W, together with other ring member atoms, forms a nitrogen-containing heterocycle selected from the group consisting of a pyridine ring, a pyrazine ring, an imidazole ring, an oxazole ring, a thiazole ring, a quinoline ring, an isoquinoline ring, a quinoxaline ring, a phenanthroline ring, a pteridine ring, and an azocine ring, X is —O— or —NH—, Y is selected from the group consisting of a substituted or unsubstituted C1-C20 alkyl group, a substituted or unsubstituted C2-C20 alkenyl group, a substituted or unsubstituted C2-C20 alkynyl group, a substituted or unsubstituted C3-C20 cycloalkyl group, a substituted or unsubstituted C3-C20 cycloalkenyl group, a substituted or unsubstituted C6-C20 aryl group, a substituted or unsubstituted C3-C20 heteroaryl group, and a monovalent group derived from a substituted or unsubstituted aliphatic heterocycle having an electron-withdrawing property, Z represents a hydrogen atom or an electron-withdrawing substituent present on the nitrogen-containing heterocycle, p, q and r are each independently 0 or 1, s represents an integer of 0 to 10, $L^0$ and $L^1$ each independently represent a linker having a chemically stable structure, $A^a$ and $A^b$ are each independently a group selected from the group consisting of —CH=CH—, —C(=O)—, —C(=O)—O—, —O—C(=O)—, —O—, C1-C20 oxyalkylene, C1-C20 alkyleneoxy, —C(=O)—NH—, —NH—C(=O)—, —NH—C(=O)—NH—, hydrazine, triazole, sulfone, sulfoxide, sulfonic acid ester, sulfonamide, sulfinic acid ester, sulfinamide, piperidine and dioxane, s represents an integer of 0 to 10, and R is a hydrogen atom, a substituted or unsubstituted C1-C20 alkyl group, a substituted or unsubstituted C2-C20 alkenyl group, a substituted or unsubstituted C2-C20 alkynyl group, a substituted or unsubstituted C3-C20 cycloalkyl group, a substituted or unsubstituted C3-C20 cycloalkenyl group, a substituted or unsubstituted C6-C20 aryl group, a substituted or unsubstituted C3-C20 heteroaryl group, an amino group, a hydroxy group, or a polymer carrier;

provided that the following compounds are excluded from the range of the nitrogen-containing compound:

(A) 3-nitro-2-pyridine sulfinic acid methyl,
(B) 3-nitro-2-pyridine sulfinic acid ethyl,
(C) 3-nitro-2-pyridine sulfinic acid N,N-diethylaminoethyl,
(D) N-(3'-nitro-2'-pyridinesulfenyloxy)-5-norbornene-2,3-dicarboximide,
(E) (S)-((tert-butoxycarbonyl)amino)-3-(((3-nitropyridin-2-yl)thio)oxy)propanoic acid,
(F) (2S,3R)-2-(((benzyloxy)carbonyl)amino)-3-(((3-nitropyridin-2-yl)thio)oxy)butanoic acid,
(G) 4-(((3-nitropyridin-2-yl)thio)oxy)methyl)benzoic acid, and
(H) (S)-2-(((3-nitropyridin-2-yl)thio)oxy)-3-phenylpropanoic acid.

In addition, according to another aspect of the present invention, there is provided a disulfidation reagent for a thiol group including the above-described nitrogen-containing compound or a salt thereof, or any one of the above compounds (A) to (H). Here, the above compounds (A) to (H) (3-nitro-2-pyridine sulfinic acid derivative) are known compounds. However, it has not been previously known whether the compound is capable of functioning as a disulfidation reagent for a thiol group.

Further, according to still another aspect of the present invention, there is provided a method for producing a disulfide-containing compound including contacting a compound having two or more free thiol groups in a molecule with the above-described disulfidation reagent to form a disulfide bond between the two free thiol groups, thereby obtaining a disulfide-containing compound.

In addition, according to still another aspect of the present invention, there is provided a method for producing the above-described nitrogen-containing compound or a salt thereof.

Advantageous Effects of Invention

According to the present invention, there is provided a means capable of selectively introducing a disulfide bond with respect to two free thiol groups located in a molecule of an organic compound such as a peptide, or the like, in a relatively short time by a simple treatment and also by a chemically stable method.

BRIEF DESCRIPTION OF DRAWINGS

FIG. 1 is a chart showing HPLC analysis results of the reaction system before an addition of Compound 2a (A), 1 hour after the addition (B), and 6 hours after the addition (C) when peptide 4 is synthesized from peptide 3 in Example 2-1 described below.

FIG. 2 is a chart showing HPLC analysis results of the reaction system before an addition of Compound 2a (A), 1 hour after the addition (B), 6 hours after the addition (C), and 24 hours after the addition (D) when peptide 6 is synthesized from peptide 5 in Example 2-2 described below.

FIG. 3 is a chart showing HPLC analysis results of the reaction system before an addition of Compound 2a (A), 4 hours after the addition (B), 9 hours after the addition (C), and 27 hours after the addition (D) when peptide 8 is synthesized from peptide 7 in Example 2-3 described below.

FIG. 4 is a chart showing HPLC analysis results of the reaction system before an addition of iodine (A), 2 minutes after the addition (B), 1 hour after the addition (C), and after HPLC purification (D) when peptide 9 is synthesized from peptide 8 in Example 2-3 described below.

FIG. 5 is a chart showing results of HPLC analysis performed on (A) α-conotoxin ImI (peptide 9) synthesized in Example 2-3 to be described below, (B) a commercially available standard sample α-conotoxin ImI, and (C) a mixed sample thereof, respectively.

DESCRIPTION OF EMBODIMENTS

Figure 6:
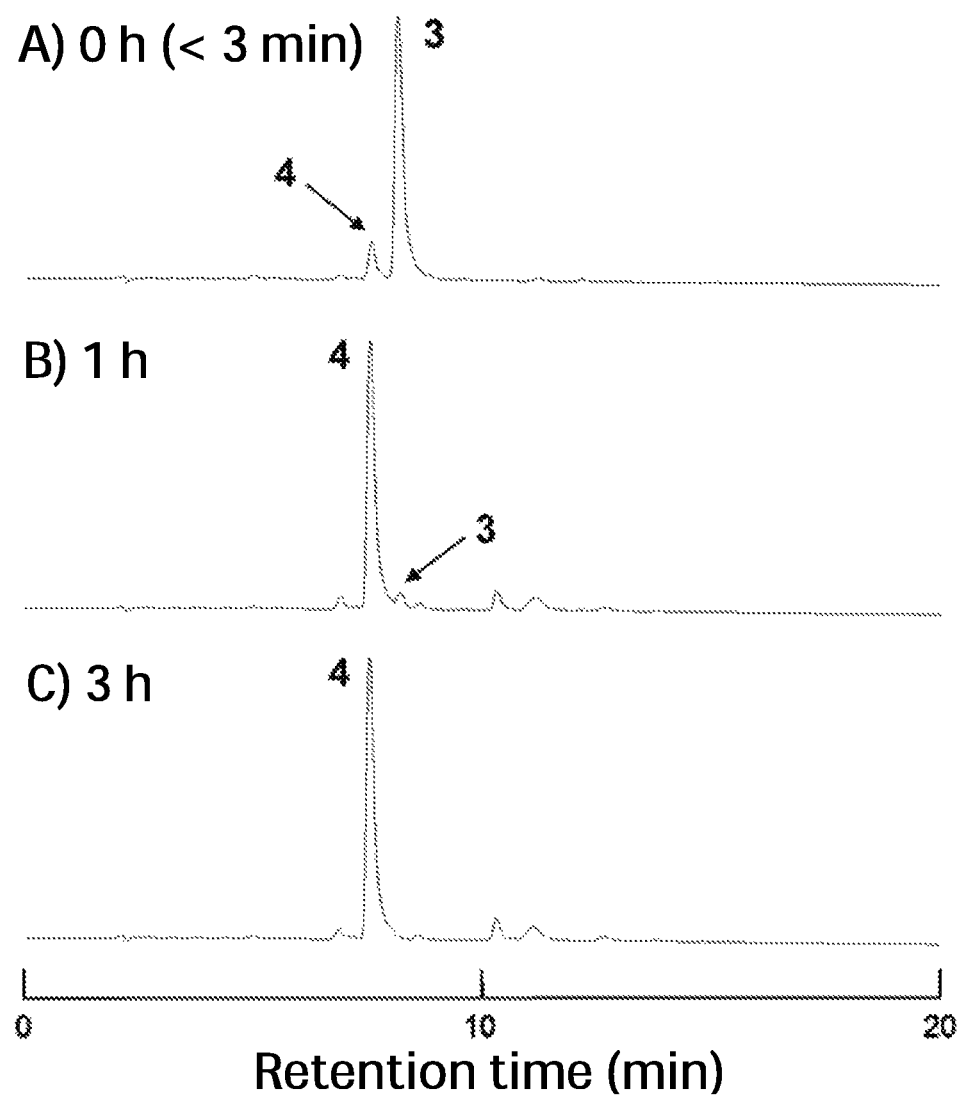
FIG. 6 is a chart showing HPLC analysis results of the reaction system within 3 minutes from the start of the reaction (A), after 1 hour from the start of the reaction (B), and after 3 hours from the start of the reaction (C) when peptide 4 is synthesized from peptide 3 using a solid phase disulfidation reagent (Compound 11) in Example 3-2 described below.

Hereinafter, exemplary embodiments of the present invention are described.

An aspect of the present invention relates to a novel nitrogen-containing compound, and specifically, a nitrogen-containing compound represented by Chemical Formula 1 below or a salt thereof.

[Chemical Formula 1]

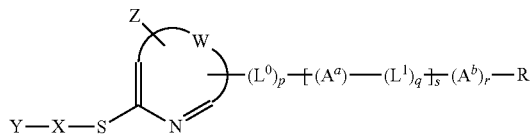

In Chemical Formula 1, W, together with other ring member atoms, forms a nitrogen-containing heterocycle selected from the group consisting of a pyridine ring, a pyrazine ring, an imidazole ring, an oxazole ring, a thiazole ring, a quinoline ring, an isoquinoline ring, a quinoxaline ring, a phenanthroline ring, a pteridine ring, and an azocine ring. Here, W, together with other ring member atoms, preferably forms a pyridine ring as the nitrogen-containing heterocycle.

In Chemical Formula 1, X is —O— or —NH—. Among them, X is preferably —O—.

In Chemical Formula 1, Y is selected from the group consisting of a substituted or unsubstituted C1-C20 alkyl group, a substituted or unsubstituted C2-C20 alkenyl group, a substituted or unsubstituted C2-C20 alkynyl group, a substituted or unsubstituted C3-C20 cycloalkyl group, a substituted or unsubstituted C3-C20 cycloalkenyl group, a substituted or unsubstituted C6-C20 aryl group, a substituted or unsubstituted C3-C20 heteroaryl group, and a monovalent group derived from a substituted or unsubstituted aliphatic heterocycle having an electron-withdrawing property. Here, "the monovalent group derived from an aliphatic heterocycle having an electron-withdrawing property" corresponds to an aliphatic heterocyclic compound having an electron-withdrawing structure, or the like, and for example, may be a monovalent group in which a hydroxy group is removed from an alcohol forming an active ester of a carboxylic acid in the peptide synthesis. More specifically, the monovalent group described in Tables 5.7 to 5.11 in pages 164-173 of The Second series of pharmaceutical research and development (No. 14, Peptide Synthesis) (Hirokawa-Shoten Ltd.) or a monovalent group derived from a compound described on the same page, may be included. In addition, specific examples of these groups are described as follows.

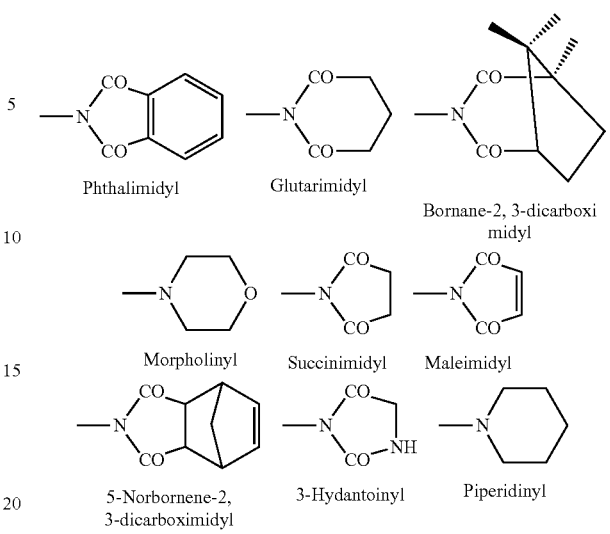

Among them, the "monovalent group derived from an aliphatic heterocycle having an electron-withdrawing property" is preferably a substituted or unsubstituted succinimidyl group, maleimidyl group, phthalimidyl group, or a 5-norbornene-2,3-dicarboximidyl group. Further, Y is preferably a substituted or unsubstituted C1-C20 alkyl group, or a substituted or unsubstituted C6-C20 aryl group, more preferably a substituted or unsubstituted C1-C20 alkyl group, more preferably an unsubstituted C1-C20 alkyl group, still more preferably an unsubstituted C1-C12 alkyl group, more preferably an unsubstituted C1-C8 alkyl group, particularly preferably an unsubstituted C1-C4 alkyl group, and the most preferably a methyl group.

In the present specification, examples of the alkyl group may include a methyl group, an ethyl group, an n-propyl group, an isopropyl group, an n-butyl group, an isobutyl group, a sec-butyl group, a tert-butyl group, a n-pentyl group, an isopentyl group, a neopentyl group, a 1,2-dimethylpropyl group, an n-hexyl group, a 1,3-dimethylbutyl group, a 1-isopropylpropyl group, a 1,2-dimethylbutyl group, a n-heptyl group, a 1,4-dimethylpentyl group, a 2-methyl-1-isopropylpropyl group, a 1-ethyl-3-methylbutyl group, a n-octyl group, a 2-ethylhexyl group, a 3-methyl-1-isopropylbutyl group, a 2-methyl-1-isopropyl group, a 1-tert-butyl-2-methylpropyl group, a n-nonyl group, a 3,5,5-trimethylhexyl group, and the like.

In the present specification, examples of the alkenyl group may include a vinyl group, an allyl group, an isopropenyl group, a 1-butenyl group, a 2-butenyl group, a 2-methyl-2-propenyl group, a 1-methyl-2-propenyl group, a 2-methyl-1-propenyl group, a pentenyl group, a 1-hexenyl group, a 3,3-dimethyl-1-butenyl group, and the like.

In the present specification, examples of the alkynyl group may include an ethynyl group, a 1-propynyl group, a 2-propynyl group, a 1-butynyl group, a 2-butynyl group, a 3-butynyl group, a 3-methyl-1-propynyl group, a 2-methyl-3-propynyl group, a pentynyl group, a 1-hexynyl group, a 3-methyl-1-butynyl group, a 3,3-dimethyl-1-butynyl group, and the like.

In the present specification, examples of the cycloalkyl group may include a cyclobutyl group, a cyclopentyl group, a cyclohexyl group, a cycloheptyl group, a cyclooctyl group, and the like.

In the present specification, examples of the cycloalkenyl group may include a cyclobutenyl group, a cyclopentenyl group, a cyclohexenyl group, and the like.

In the present specification, examples of the aryl group may include a phenyl group, a 1-naphthyl group, a 2-naphthyl group, a 1-anthracenyl group, a 2-anthracenyl group, a 9-anthracenyl group, and the like.

In the present specification, examples of the heteroaryl group may include a 2-thienyl group, a 4-pyridyl group, a 3-pyridyl group, a 2-pyridyl group, a 1-pyridyl group, a 2-furyl group, a 2-pyrimidinyl group, a 2-benzothiazolyl group, a 1-imidazolyl group, a 1-pyrazolyl group, a benzotriazol-1-yl group, a 7-azabenzotriazol-1-yl group, and the like.

Further, in the present specification, when a group is "substituted", examples of a substituent capable of substituting the group may include halogen atoms such as fluorine, chlorine, bromine, iodine, and the like, an alkyl group, an aryl group, an alkoxy group, an aryloxy group, an alkoxycarbonyl group, an acyloxy group, an acyl group, an alkylsulfanyl group, an arylsulfanyl group, an alkylamino group, a dialkylamino group, an arylamino group, a hydroxy group, a carboxyl group, a formyl group, a mercapto group, a sulfo group, a sulfinic acid group, a guanidino group, a carbamoyl group, a thiol group, a thioether group, a mesyl group, a p-toluenesulfonyl group, an amino group, a nitro group, a cyano group, a trifluoromethyl group, a trichloromethyl group, a trimethylsilyl group, a phosphinico group, a phosphono group, and the like. These substituents may also be further substituted with a halogen atom, an alkyl group, an aryl group, an alkoxy group, a hydroxy group, a carboxy group, an amino group, a nitro group, a cyano group, and the like. Provided that substitution included in the definition in which a group after substitution is the same as a group before substitution is not considered.

In Chemical Formula 1, Z represents a hydrogen atom or an electron-withdrawing substituent present on the nitrogen-containing heterocycle, and is preferably an electron-withdrawing substituent. Here, examples of the electron-withdrawing substituent may include a nitro group, a trifluoromethyl group, a halogen atom (fluorine atom, chlorine atom, bromine atom, and iodine atom), an acetyl group, a methanesulfonyl group, a trifluoroacetyl group, a trifluoromethane sulfonyl group, a cyano group, and the like.

Among them, a nitro group, a trifluoromethyl group or a halogen atom is preferable, and a nitro group is the most preferable.

In Chemical Formula 1, p is 0 or 1. When p is 0, $L^0$ is absent and $A^a$ or $A^b$ or R is directly bonded to the nitrogen-containing heterocycle, and when p is 1, $L^0$ is present.

In Chemical Formula 1, q is 0 or 1. When q is 0, $L^1$ is absent, and when q is 1, $L^1$ is present.

In Chemical Formula 1, r is 0 or 1. When r is 0, $A^b$ is absent, and when r is 1, $A^b$ is present.

In Chemical Formula 1, s is an integer of 0 to 10. When S is 0, $[(A^a)-(L^1)_q]$ is absent, and when s is an integer of 1 to 10, $[(A^a)-(L^1)_q]$ is present repeatedly by s times. In addition, s is preferably 0 to 5, and more preferably 0 or 1.

$L^0$ and $L^1$, if present, each independently represent a linker having a chemically stable structure. The linker is not particularly limited in view of a specific structure, and may be, for example, a substituted or unsubstituted C1-C20 alkylene group, a substituted or unsubstituted C2-C20 alkenylene group, a substituted or unsubstituted C2-C20 alkynylene group, a substituted or unsubstituted C3-C20 cycloalkylene group, a substituted or unsubstituted C3-C20 cycloalkenylene group, a substituted or unsubstituted C6-C20 arylene group, a substituted or unsubstituted C3-C20 heteroarylene group, —NH—, —O—, —S—, —C(=O)—NH—, —NH—C(=O)—, —O—, —C(=O)—O—, —O—C(=O)—, —S—, —C(=O)—, and a polyoxyalkylene group. Further, $L^0$ and $L^1$ may be groups represented by Chemical Formula (a) below.

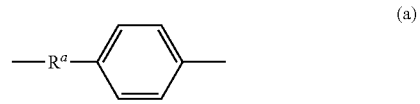

(a)

In Chemical Formula (a), $R^a$ represents a substituted or unsubstituted C1-C15 alkylene group, preferably a C1-C8 alkylene group, more preferably a C1-C4 alkylene group, particularly preferably a C1-C2 alkylene group, and most preferably a C2 alkylene group (particularly an ethylene group). As $L^0$ and $L^1$, a C1-C6 alkylene group (particularly an ethylene group), a polyoxyalkylene group having a molecular weight of 100 to 1000, or a group represented by Chemical Formula (a) above is preferably used.

In Chemical Formula 1, $A^a$ and $A^b$, if present, are each independently a group selected from the group consisting of —CH=CH—, —C≡C—, —C(=O)—, —C(=O)—O—, —O—C(=O)—, —O—, C1-C20 oxyalkylene, C1-C20 alkyleneoxy, —C(=O)—NH—, —NH—C(=O)—, —NH—C(=O)—NH—, hydrazine, triazole, sulfone, sulfoxide, sulfonic acid ester, sulfonamide, sulfinic acid ester, sulfinamide, piperidine, and dioxane. Among them, as $A^a$ and $A^b$, —C(=O)—, —C(=O)—O—, —O—, C1-C20 oxyalkylene, C1-C20 alkyleneoxy, —O—C(=O)—, —C(=O)—NH—, or —NH—C(=O)— is preferably used.

In Chemical Formula 1, R is a hydrogen atom, a substituted or unsubstituted C1-C20 alkyl group, a substituted or unsubstituted C2-C20 alkenyl group, a substituted or unsubstituted C2-C20 alkynyl group, a substituted or unsubstituted C3-C20 cycloalkyl group, a substituted or unsubstituted C3-C20 cycloalkenyl group, a substituted or unsubstituted C6-C20 aryl group, a substituted or unsubstituted C3-C20 heteroaryl group, an amino group, a hydroxy group, or a polymer carrier. The polymer carrier as R is typically a polymer carrier used in a solid phase synthesis method. The polymer carrier is selected from the group consisting of, for example, polystyrene, polypropylene, polyethylene, polyether, polyvinyl chloride, dextran, polyacrylamide, polyethylene glycol, copolymers and crosslinked products thereof, magnetic beads, and a combination thereof. The polymer carrier is more preferably a crosslinked product of polystyrene, polyethylene glycol, and polyethylene glycol. These polymer carriers may be bonded between adjacent groups (i.e., TO, $L^1$, and the like) through an alkyl group such as a methyl group, or the like. Further, a shape of the polymer carrier is not particularly limited, but is more preferably a spherical shape. In this case, an average particle diameter of the polymer carrier is preferably 100 to 400 mesh. The polymer carrier is commercially available, and for example, aminomethyl-ChemMatrix® resin manufactured by Sigma-Aldrich is known as a polymer carrier formed of a polyethylene glycol crosslinked product. Further, as the polymer carrier formed of the polystyrene resin, a resin described in pages 283-295 of The Second series of pharmaceutical research and development (No. 14, Peptide Synthesis) (Hirokawa-Shoten Ltd.) may be included. Specifically, for example, a chloromethylated (Merrifield) resin, an aminomethyl resin, a Wang resin, a Pam resin, a Rink acid resin, a Rink amide resin, an oxime resin, a 4-methylbenzhydrylamine resin, a PAL resin, a 2-chlorotrityl chloride resin, and the like, may be included.

In addition, the nitrogen-containing compound represented by Chemical Formula 1 according to the present invention may be in the form of a salt. For example, the salt may be formed between an anion and a positively charged substituent (e.g., an amino group) on the above-described compound. Here, the appropriate anion, chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, maleate, and the like. Likewise, these salts may be formed between a cation and a negatively charged substituent (e.g., a carboxyl group) on the above-described compound. Here, appropriate examples of the cation can include ammonium cations such as a sodium ion, a potassium ion, a magnesium ion, a calcium ion and a tetramethylammonium ion. The above-described compounds also include salts thereof including a quaternary nitrogen atom.

From the concept of the novel nitrogen-containing compound according to an aspect of the present invention or a salt thereof, the following compounds are excluded (i.e., the following compounds are known compounds):
(A) 3-nitro-2-pyridine sulfinic acid methyl
(B) 3-nitro-2-pyridine sulfinic acid ethyl
(C) 3-nitro-2-pyridine sulfinic acid N,N-diethylaminoethyl
(D) N-(3'-nitro-2'-pyridinesulfenyloxy)-5-norbornene-2,3-dicarboxyimide
(E) (S)—((tert-butoxycarbonyl)amino)-3-(((3-nitropyridin-2-yl)thio)oxy)propanoic acid
(F) (2S,3R)-2-(((benzyloxy)carbonyl)amino)-3-(((3-nitropyridin-2-yl)thio)oxy)butanoic acid
(G) 4-(((3-nitropyridin-2-yl)thio)oxy)methyl)benzoic acid, and
(H) (S)-2-(((3-nitropyridin-2-yl)thio)oxy)-3-phenylpropanoic acid.

Further, all of these compounds (A) to (H) correspond to compounds in which p=0, s=0, and r=0, and at the same time, R is a hydrogen atom in Chemical Formula 1 above. It is preferable that the nitrogen-containing compound according to the present aspect or a salt thereof does not satisfy the condition of "p=0, s=0, r=0, and R=hydrogen atom" in Chemical Formula 1 above.

Hereinafter, although some preferred embodiments of the nitrogen-containing compound represented by Chemical Formula 1 according to the present invention are described, the technical scope of the present invention is not limited to the following embodiments.

First Preferred Embodiment

In a first preferred embodiment of the nitrogen-containing compound represented by Chemical Formula 1 according to the present invention, q is 0, r is 0, and s is 1. Thus, the compound represented by Chemical Formula 1 is represented by Chemical Formula 2 below.

[Chemical Formula 2]

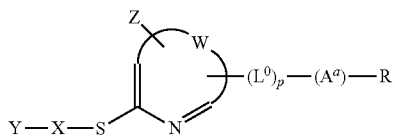

In addition, in Chemical Formula 2,

W, X, Y, Z, p, $L^0$ and $A^a$ are the same as defined above.

In addition, in the present embodiment, R is a group other than "amino group, hydroxy group, and polymer carrier", i.e., a substituted or unsubstituted C1-C20 alkyl group, a substituted or unsubstituted C2-C20 alkenyl group, a substituted or unsubstituted C2-C20 alkynyl group, a substituted or unsubstituted C3-C20 cycloalkyl group, a substituted or unsubstituted C3-C20 cycloalkenyl group, a substituted or unsubstituted C6-C20 aryl group, or a substituted or unsubstituted C3-C20 heteroaryl group.

In the present embodiment, a preferred form of each symbol (substituent) is the same as described above with respect to Chemical Formula 1. Provided that, in the present embodiment, R is preferably a substituted or unsubstituted C1-C20 alkyl group, or a substituted or unsubstituted C6-C20 aryl group, more preferably a substituted or unsubstituted C1-C20 alkyl group, more preferably an unsubstituted C1-C20 alkyl group, still more preferably an unsubstituted C1-C12 alkyl group, more preferably an unsubstituted C1-C8 alkyl group, particularly preferably an unsubstituted C1-C4 alkyl group, and the most preferably a methyl group.

Further, in the present embodiment, $A^a$ is preferably selected from the group consisting of —C(=O)—, —C(=O)—O—, —O—C(=O)—, —O—, —C(=O)—NH—, and —NH—C(=O)—, more preferably selected from the group consisting of —C(=O)—O—, —O—C(=O)—, —C(=O)—NH—, and —NH—C(=O)—, particularly preferably —C(=O)—O— or —O⁻C(=O)—, and the most preferably —C(=O)—O—.

In addition, in the present embodiment, p may be 0 or 1, but preferably p is 0 (i.e., it is preferred that $L^0$ is absent and $A^a$ is directly bonded to the aromatic heterocycle).

Examples of the compound according to the present embodiment are as follows.

Compound 2a

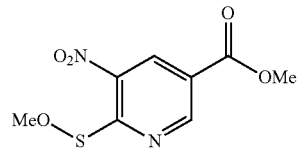

Example 1-1 to be described

Compound 2b

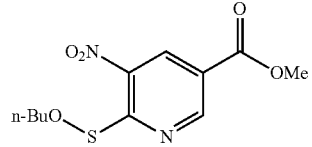

Example 1-2 to be described

Compound 2c

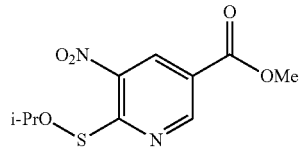

Example 1-3 to be described

-continued

Compound 2d

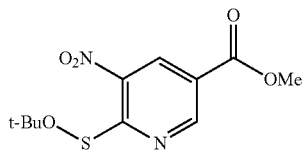

Example 1-4 to be described

Compound 2e

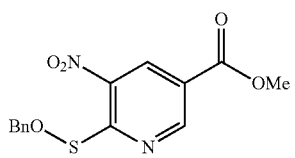

Example 1-5 to be described

Compound 2f

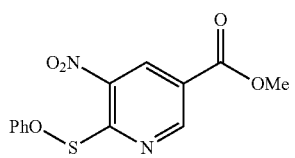

Example 1-6 to be described

Compound 2g

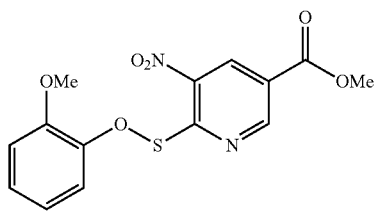

Example 1-7 to be described

Compound 2h

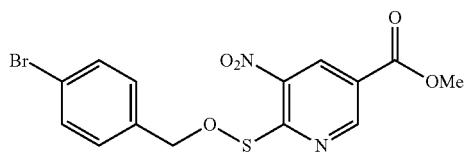

Example 1-8 to be described

Compound 2i

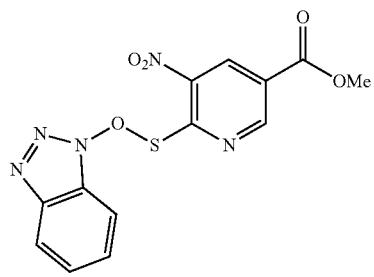

Example 1-9 to be described

Second Preferred Embodiment

In a second preferred embodiment of the nitrogen-containing compound represented by Chemical Formula 1 according to the present invention, q is 0, r is 0, and s is 1. Thus, the compound represented by Chemical Formula 1 is represented by Chemical Formula 3 below, as in Chemical Formula 2 above.

[Chemical Formula 3]

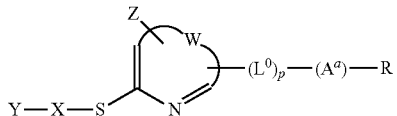

In addition, in Chemical Formula 3, W, X, Y, Z, p, $L^0$, and $A^a$ are the same as defined in Chemical Formula 1 above, as in Chemical Formula 2 above. Meanwhile, in the present embodiment, R is a polymer carrier. Here, in the present embodiment, a preferred form of each symbol (substituent) is the same as described above with respect to Chemical Formula 1.

However, in the present embodiment, a preferred form of R, which is a polymer carrier, is a polyethylene glycol crosslinked product (e.g., aminomethyl ChemMatrix® resin). In this case, $A^a$ is preferably —C(=O)—NH—. In addition, in this case, p may be 0 or 1, but preferably p is 0 (i.e., it is preferred that $L^0$ is absent and $A^a$ is directly bonded to the aromatic heterocycle). An example of the preferred compound in the present embodiment is the following compound 11.

[Compound 11]

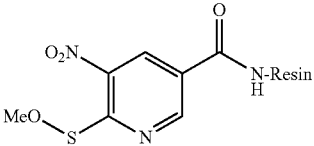

[Example 3-1 to be described below]

Resin: Crosslinked Product of Polyethylene Glycol (MethylChemMatrix® Resin)

Likewise, in the present embodiment, another preferred form of R, which is a polymer carrier, is a polystyrene resin. In this case, $A^a$ is preferably —C(=O)—O—. In addition, in this case, p may be 0 or 1, but preferably p is 0 (i.e., it is preferred that $L^0$ is absent and $A^a$ is directly bonded to the aromatic heterocycle). An example of a preferred compound in the present embodiment is Compound 12 below.

[Compound 12]

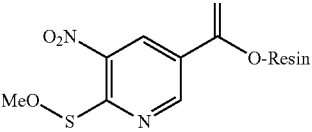

Resin: Polystyrene Resin

Third Preferred Embodiment

In a third preferred embodiment of the nitrogen-containing compound represented by Chemical Formula 1 according to the present invention, q is 1, r is 1, and s is 1. Thus, the compound represented by Chemical Formula 1 is represented by Chemical Formula 4 below.

[Chemical Formula 4]

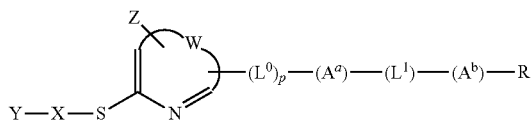

In addition, in Chemical Formula 4, W, X, Y, Z, p, $L^0$, $L^1$, $A^a$, and $A^b$ are the same as defined in Chemical Formula 1 above. Meanwhile, in the present embodiment, R is a polymer carrier.

Here, in the present embodiment, a preferred form of each symbol (substituent) is the same as described above with respect to Chemical Formula 1.

Provided that in the present embodiment, it is preferred that $A^a$ and $A^b$ are —C(=O)—NH—, $L^1$ is a C1-C20 alkylene group, and R, which is a polymer carrier, is a polyethylene glycol crosslinked product (e.g., aminomethyl ChemMatrix® resin). In addition, in this case, p may be 0 or 1, but preferably p is 0 (i.e., it is preferred that $L^0$ is absent and $A^a$ is directly bonded to the aromatic heterocycle). An example of a preferred compound in the present embodiment is the following Compound 13 (in Compound 13, $L^1$ is a C5 alkylene group (pentamethylene group)).

[Compound 13]

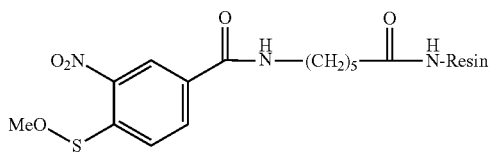

Resin: Crosslinked Product of Polyethylene Glycol (MethylChemMatrix® Resin)

As described above, although several preferred embodiments of the nitrogen-containing compound represented by Chemical Formula 1 according to the present invention are described, the compound represented by Chemical Formula 1 according to the present invention may be other compounds than these exemplified compounds. Examples of compounds that are not included in the above-described embodiments, include, for example, the following compounds 14 and 15 without limitation:

[Compound 14]

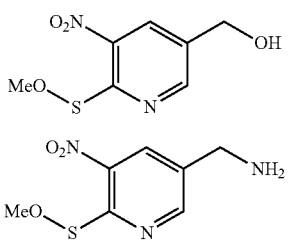

[Compound 15]

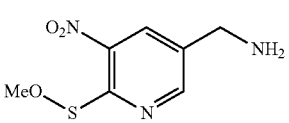

(Method for Producing the Compound of Present Invention)

The method for producing the nitrogen-containing compound according to the present invention is not particularly limited. A person skilled in the art can produce the compound according to the present invention in consideration of the technical knowledge at the time when the present application was filed, on the basis of the description of Examples to be described below. Hereinafter, a method for producing a compound where X is —O— in Chemical Formula 1 above among the compounds according to the present invention is described.

A starting material in the production method according to the present embodiment is a compound represented by Chemical Formula 5 below.

[Chemical Formula 5]

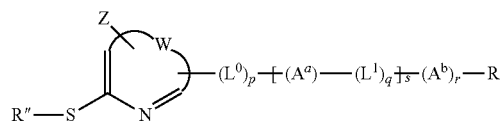

In Chemical Formula 5, W, Z, p, q, r, s, $L^0$, $L^1$, $A^a$, and $A^b$ are the same as defined in Chemical Formula 1 above.

In addition, in Chemical Formula 5, R" is a leaving group. The specific type of the leaving group constituting R" is not particularly limited and conventionally known leaving groups can be used, and examples thereof can include a benzyl group, a methoxybenzyl group, a dimethylamino benzyl group, a trityl group, a chlorotrityl group, a methyltrityl group, a methoxytrityl group, a tert-butyl group, and the like.

The compound represented by Chemical Formula 5 can be synthesized, for example, as described in the International Publication No. 2015/050199.

In the production method according to the present embodiment, the starting material prepared above (a compound represented by Chemical Formula 5) reacts with halogen simple substance or a halogen generating reagent (e.g., sulfuryl chloride, chlorine gas, phosphorus oxychloride, phosphorus pentachloride, bromine, fluorinated alkylpyridine, fluorinated quinuclidine or iodine). Thus, a compound represented by Chemical Formula 6 below is obtained (step (1)).

[Chemical Formula 6]

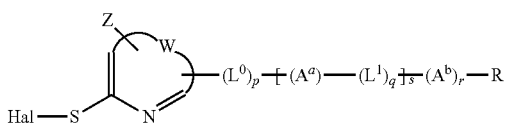

Here, in Chemical Formula 6, W, Z, p, q, r, s, $L^0$, $L^1$, $A^a$, and $A^b$ are the same as defined in Chemical Formula 1 above.

In addition, in Chemical Formula 6, Hal represents a halogen atom selected from fluorine, chlorine, bromine or iodine.

When the above reaction is performed in the step (I), for example, a halogen generating reagent such as pyridine, sulfuryl chloride, or the like, in addition to a solvent such as 1,2-dichloroethane or the like, is added to the compound represented by Chemical Formula 5, and the obtained reaction product was stirred for 1 to 2 hours gently. Thereafter, the reaction solution can be distilled off under reduced pressure and subjected to azeotropy with hexane or the like. Here, when R is a polymer carrier, it is preferred to swell the compound represented by Chemical Formula 5 with a solvent before the reaction in advance.

In the production method according to the present embodiment, subsequently, the compound represented by Chemical Formula 6 obtained above reacts with an alcohol represented by Y—OH (Y is the same as defined in Chemical Formula 1) under basic conditions. Thus, a compound represented by Chemical Formula 7 below is obtained (step (II)).

[Chemical Formula 7]

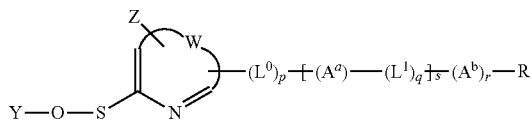

Here, in Chemical Formula 7, W, Y, Z, p, q, r, s, $L^0$, $L^1$, $A^a$, and $A^b$ are the same as defined in Chemical Formula 1 above. Further, the compound represented by Chemical Formula 7 above corresponds to a compound where X is —O— in Chemical Formula 1 above.

When the above reaction is performed in step (I), for example, the compound represented by the above-obtained compound 6 is dissolved in an alcohol represented by Y—OH. In addition, when a base is added while stirring the reaction system, a nucleophilic substitution reaction, in which an alkoxide ion represented by Y—O⁻ acts as a nucleophilic agent and a halide ion represented by Hal⁻ is eliminated, proceeds on the sulfur atom. As a result, the compound represented by Chemical Formula 7 above is produced. Further, the type of the base to be added is not particularly limited, but a low nucleophilic base such as N,N-diisopropylethylamine (DIPEA; Hunig's base), or the like, is preferably used since the lower nucleophilicity is preferable. The obtained product can be purified by a conventional method.

As described above, the method for producing the compound according to the present invention has been described by exemplifying the compound in which X is —O— in Chemical Formula 1 (compound represented by Chemical Formula 7), but other compounds can also be appropriately produced by a person skilled in the art. For example, the compound where X is —NH— in Chemical Formula 1 may be produced by reacting the compound represented by Chemical Formula 6 obtained above with an amine represented by Y—NH₂ in a suitable organic solvent, through the same reaction mechanism.

(Use of Compound of Present Invention)

The present inventors surprisingly found that the above-described nitrogen-containing compound (or salt thereof) of the present invention had a function as a disulfidation reagent. It was also found that the nitrogen-containing compound according to the present invention was chemically extremely stable as it was capable of being stored at room temperature (25° C.). Further, by using the nitrogen-containing compound according to the present invention as the disulfidation reagent, an excellent effect is shown, in which it is possible to selectively introduce a disulfide bond into two free thiol groups located in a molecule of an organic compound such as a peptide or the like, in a short time by a simple process and by a chemically stable method, which is not exhibited by the conventionally known disulfidation reagent. Further, even as to the above-described compounds (A) to (H) as known compounds, the use of the disulfidation reagent of the thiol group described above has not been known. However, according to the present invention, the invention of use as the disulfidation reagent is also provided with respect to these compounds (A) to (H). Thus, according to another embodiment of the present invention, there is provided a disulfidation reagent for a thiol group including the above-described nitrogen-containing compound or a salt thereof, or the following compounds (A) to (H):

(A) 3-nitro-2-pyridine sulfinic acid methyl
(B) 3-nitro-2-pyridine sulfinic acid ethyl
(C) 3-nitro-2-pyridine sulfinic acid N,N-diethylaminoethyl
(D) N-(3'-nitro-2'-pyridinesulfenyloxy)-5-norbornene-2,3-dicarboxyimide
(E) (S)-(((tert-butoxycarbonyl)amino)-3-(((3-nitropyridin-2-yl)thio)oxy)propanoic acid
(F) (2S,3R)-2-(((benzyloxy)carbonyl)amino)-3-(((3-nitropyridin-2-yl)thio)oxy)butanoic acid
(G) 4-(((3-nitropyridin-2-yl)thio)oxy)methyl)benzoic acid, and
(H) (S)-2-(((3-nitropyridin-2-yl)thio)oxy)-3-phenylpropanoic acid.

Here, as described above, it is preferable that the nitrogen-containing compound represented by Chemical Formula 1 according to the present invention does not satisfy the condition of "p=0, s=0, r=0, and R=hydrogen atom" in Chemical Formula 1 above. On the other hand, the compound satisfying this condition has a novel use as the disulfidation reagent. Thus, a preferred embodiment of the disulfidation reagent according to the present invention includes a compound, which satisfies that "p=0, s=0, r=0 and R=hydrogen atom (Chemical Formula 8 below)" in Chemical Formula 1 above among the nitrogen-containing compounds represented by Chemical Formula 1 according to the present invention, as an active ingredient:

[Chemical Formula 8]

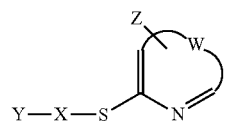

In Chemical Formula 8, W, X, Y and Z are the same as defined in Chemical Formula 1 above. Here, preferred forms of respective symbols (substituents) are the same as described above in Chemical Formula 1.

In an example of the preferred disulfidation reagent in the present embodiment, any one of the following compounds 14a to 14j is included as an active ingredient:

Compound 16a

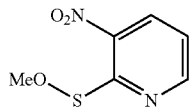

Example 4-1 to be described below

Compound 16b

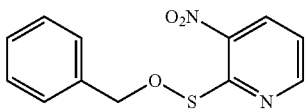

Example 4-2 to be described below

-continued

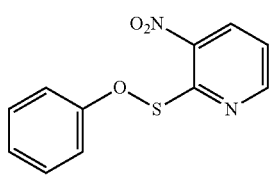

Example 4-3 to be described below

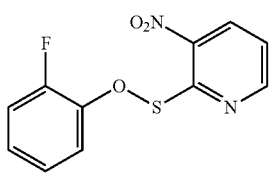

Example 4-4 to be described below

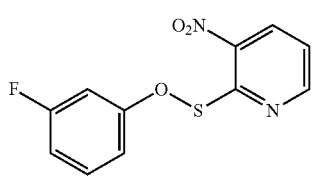

Example 4-5 to be described below

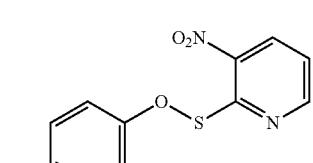

Example 4-6 to be described below

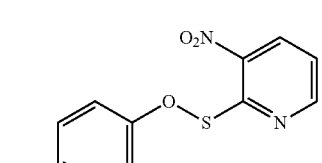

Example 4-7 to be described below

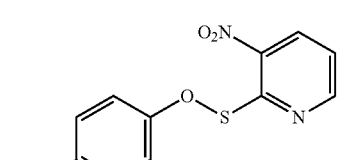

Example 4-8 to be described below

-continued

Compound 16c

Compound 16d

Compound 16e

Compound 16f

Compound 16g

Compound 16h

Compound 16i

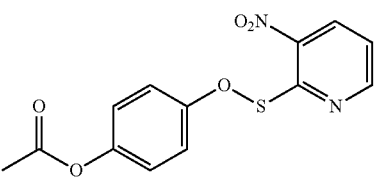

Example 4-9 to be described below

Compound 16j

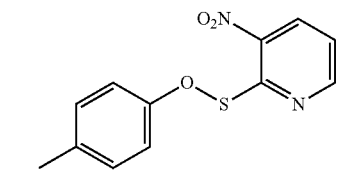

Example 4-10 to be described below

Further, when R in the above-described Chemical Formula 1 is a polymer carrier used in the solid phase synthesis method, the nitrogen-containing compounds having a disulfidation activity can be immobilized on the polymer carrier used in the solid phase synthesis method. Therefore, in this case, the polymer carrier can be used as a solid phase supported reagent which selectively acts on two free thiol groups located in the molecule of an organic compound such as peptide, or the like.

Still another aspect of the present invention relates to a method for introducing a disulfide bond (—S—S—) into a compound having two or more free thiol groups in the molecule using the nitrogen-containing compound according to the present invention described above as the disulfidation reagent (preferably, a solid phase supported disulfidation reagent). In other words, the method according to the present aspect is a method for producing a disulfide-containing compound including contacting a compound having two or more free thiol groups in a molecule with the disulfidation reagent comprised of the nitrogen-containing compound (or a salt thereof) according to the present invention described above to form a disulfide bond between the two free thiol groups, thereby obtaining a disulfide-containing compound.

Here, the structure of the "compound having two or more free thiol groups in the molecule", which is a subject to which the disulfide bond is introduced, is not particularly limited. Examples of the "compounds having two or more free thiol groups in the molecule" can include a high molecular weight compound, a low molecular weight compound, and a derivative including an isotope thereof, in addition to the amino acid residue-containing compound such as an amino acid, a peptide (including oligopeptide, polypeptide (including proteins such as an antibody, and the like)), or the like. Further, the existing form of the free thiol group in the compound is not particularly limited. For example, the free thiol group may be a cystein amino group, a thioalkylamino group, or the like, in an organic compound, in addition to the cysteine residue and the cysteine amide residue in the amino acid, the peptide or the protein.

When the "compound having two or more free thiol groups in the molecule" is a peptide, the peptide may be derived naturally or artificially synthesized. When the peptide is artificially synthesized, there is no particular limitation on the synthesis method thereof, and conventionally known knowledge can be appropriately referred. As an artificial synthesis method of peptide, a "solid phase synthesis method" and a "liquid phase synthesis method" are known, and in the case of the solid phase synthesis method, the Fmoc method and Boc method are further known. When the "compound having two or more free thiol groups in the molecule" is a peptide, the peptide may be synthesized by any method. Briefly explaining by way of example of the solid phase synthesis method, for example, beads of a polystyrene polymer gel having a diameter of about 0.1 mm modified on a surface thereof with an amino group are used as a solid phase, N,N'-diisopropylcarbodiimide is used as a condensation agent. Here, by using 1-hydroxybenzotriazole in combination, it is possible to suppress racemization while improving a reaction rate. Specifically, first, the amino group of the C-terminal amino acid is protected with Fmoc group or Boc group to form a peptide bond with the amino group of the polystyrene polymer gel. Next, the solid phase is washed thoroughly with a solvent, and residual reagents and amino acids are washed and removed. Thereafter, the protecting group of the amino group of the amino acid bonded to the solid phase is removed. Subsequently, the peptide is synthesized on the solid phase by sequentially repeating the same reaction using the amino acid in which the amino group is protected with the Fmoc group or the Boc group. Finally, the solid phase can be subjected by warm extraction with trifluoroacetic acid (TFA) to separate the peptide from the solid phase, thereby synthesizing the peptide.

Further, the "compound having two or more free thiol groups in the molecule" which is a subject to which the disulfide bond is introduced by the above-described method is preferably "a compound having two free thiol groups in the molecule". According to such a form, it is possible to form the disulfide bond between the two free thiol groups of the "compound having two free thiol groups in the molecule", and thus it is possible to produce a desired disulfide-containing compound with high yield and high purity. Even when the subject to which the disulfide bond is introduced is the "compound having two free thiol groups in the molecule", in the case where the compound is a peptide, there is a possibility to include three or more cysteine residues or cysteine amide residues. Therefore, in order to make the subject to which the disulfide bond is introduced to be the "compound having two free thiol groups in the molecule" in such a case, it is necessary to protect one or more thiol groups of the cysteine residue or the cysteine amide residue with a protecting group. Introduction of such a protecting group can be generally achieved by introducing the amino acid in which the thiol group is protected at a desired position during the synthesis of the peptide as described above. Further, examples of the protecting group in the thiol group in the "thiol group-protected amino acid" used in the synthesis of peptide in this method can include a t-butyl group, a trityl group, a benzhydryl group, a benzyl group, a methylbenzyl group, a dimethylbenzyl group, a trimethylbenzyl group, a methoxybenzyl group, a dimethoxybenzyl group, a trimethoxybenzyl group, a nitrobenzyl group, an acetamidomethyl group, a 9-fluorenylmethyl group, a carbonylbenzyloxy group, a diphenylbenzyl group, an ethylcarbamoyl group, a picolyl group, a sulfonyl group, or a salt thereof.

Next, a method for performing disulfidation (producing a disulfide-containing compound) is described by explaining a case where the disulfidation reagent according to the present invention is a solid phase supported disulfidation reagent, as an example.

First, "a compound having two (or more) free thiol groups in a molecule", which is a subject to which the disulfide bond is introduced, is dissolved in a solvent. According to a preferred embodiment, the compound is dissolved in water or an organic solvent containing 1% (v/v) or more of water. In addition, the pH is preferably around neutral, preferably pH 6.5 to 8.5. Further, a buffer solution can be used instead of water, and any one of water, a buffer solution and an organic solvent may be used in combination. Meanwhile, when an organic solvent is used in combination, an organic solvent blended with water is preferred, and examples thereof can include acetonitrile, dimethylformamide, acetone, dimethylsulfoxide, alcohol, tetrahydrofuran, 1,4-dioxane, and the like.

Next, a solution of the "compound having two (or more) free thiol groups in the molecule" prepared above is blended with the solid phase supported disulfidation reagent of the present invention. In this case, the solid phase supported disulfidation reagent according to the present invention may be added to a container containing the solution, or a solution may be added to a container containing the solid phase supported disulfidation reagent according to the present invention. Further, a shape and a material of the container are not limited, but the container is preferably a stirrable container to which a filter for filtration such as a tube with a filter attached thereto, or the like, is attached. The blending may be performed by standing the container, but is preferably performed by shaking or stirring with a shaker for solid phase synthesis, a magnetic stirrer, a vortex mixer, a three-one motor, or the like.

By the reaction caused by the above-described blending, the reaction can be generally performed for 5 minutes to 2 hours. An addition amount of the solid phase supported disulfidation reagent according to the present invention used in this reaction may be increased or decreased depending on an amount of the "compound having two (or more) free thiol groups in the molecule". For example, with respect to 1 equivalent of the "compound having two (or more) free thiol groups in the molecule", it is preferable to use an excessive amount of the solid phase supported disulfidation reagent according to the present invention, and more preferably 1.2 equivalents to 10 equivalents. The reaction can be completed by determining consumption of the "compound having two (or more) free thiol groups in the molecule" in solution based on a general analytical technology. For example, applicable analytical methods can include HPLC, NMR, TLC, IR, MS spectra, titration, and the like.

In the case where a raw material compound is a peptide including three or more cysteine residues or cysteine amide residues and in the case where one or more thiol groups of the cysteine residue or the cysteine amide residue is protected by a protecting group, in some cases, it is necessary to deprotect the protecting group after introducing the disulfide bond using the solid phase supported disulfidation reagent according to the present invention. As a method of such deprotection, conventionally known methods can be used. Further, it is also possible to perform deprotection of the thiol group while simultaneously introducing an additional disulfide bond between the deprotected thiol groups, by performing deprotection treatment using, for example, iodine oxidation (see "synthesis of α-conotoxin ImI" in Examples 2-3 to be described below).

After the reaction, the solid phase supported disulfidation reagent, the disulfide-containing compound which is a target product, an unreacted "compound having two or more free thiol groups in the molecule", and the "compound having two (or more) free thiol groups in the molecule" changed as the reaction progresses are separated by filtration, and the disulfide-containing compound is obtained in the filtrate. Filtration is not limited by equipment used and a filtration method. Examples of the equipment can include a filter paper, a glass fiber, a filter aid, a filter cloth, a membrane filter, a glass filter, and the like. Examples of the filtration method can include natural filtration, suction filtration, centrifugation, decantation, and the like, and the filtration methods can be selected appropriately depending on the application and the reaction scale, respectively. As described above, by making the disulfidation reagent into the form of a solid phase reagent composed of the nitrogen-containing compound in the form of being solidified on the polymer carrier, it is possible to separate the product from the disulfidation reagent only by a simple operation called filtration. Therefore, the disulfidation reagent according to the present invention, particularly in the form of a solid phase reagent, can be said to be the invention having a very high advantage in the technical field of organic synthesis (in particular, peptide synthesis).

EXAMPLES

Hereinafter, the present invention is described by Examples below, but the scope of the present invention is not limited thereto.

Example 1

As examples of the compounds of the present invention, synthesis examples of the compounds 2a to 2i are shown below.

The compounds 2a to 2i were synthesized by the following scheme.

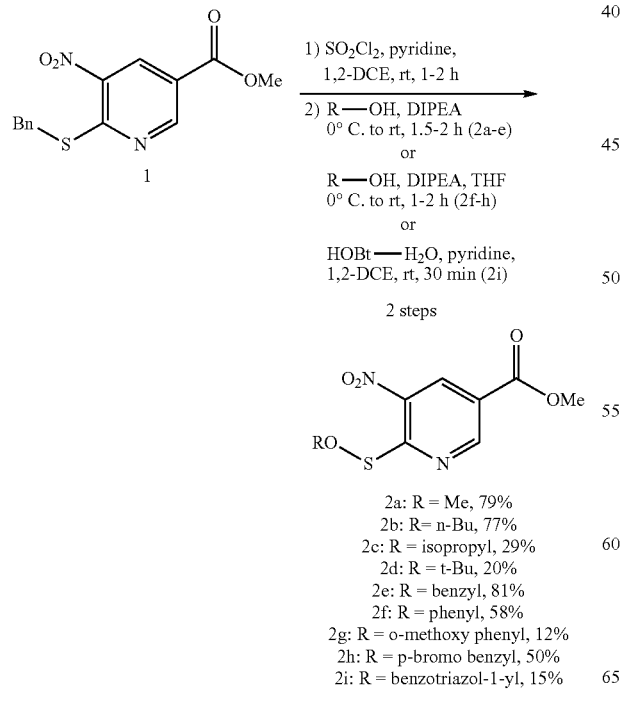

2a: R = Me, 79%
2b: R = n-Bu, 77%
2c: R = isopropyl, 29%
2d: R = t-Bu, 20%
2e: R = benzyl, 81%
2f: R = phenyl, 58%
2g: R = o-methoxy phenyl, 12%
2h: R = p-bromo benzyl, 50%
2i: R = benzotriazol-1-yl, 15%

A specific method thereof is as follows.

Example 1-1: Synthesis of Compound 2a

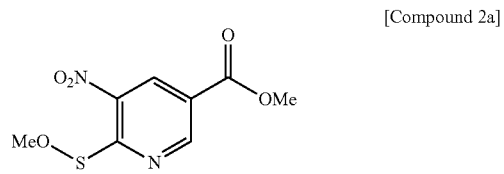 [SMILES: COSc1ncc(C(=O)OC)cc1[N+](=O)[O-]]

[Compound 2a]

Sulfuryl chloride (176 μL, 2.18 mmol) and pyridine (40.3 μL, 0.50 mmol) were added at room temperature to a solution of Compound 1 (300 mg, 0.99 mmol) in 1,2-dichloroethane (2.5 mL), and the mixture was stirred at the same temperature for 1 hour. The reaction solution was distilled off under reduced pressure and subjected to azeotropy with hexane. The obtained solution was used for the next reaction without purification. The obtained residue was dissolved in methanol (4 mL), N,N-diisopropylethylamine (2.85 mL, 19.8 mmol) was added under stirring while ice-cooling, and the mixture was stirred at room temperature for 2 hours. The reaction solution was distilled off under reduced pressure, and the obtained residue was diluted with chloroform, washed with 5% citric acid aqueous solution, water, and saturated brine, and dried over $Na_2SO_4$. After filtration, the mother liquid was distilled off under reduced pressure, and the obtained residue was purified by silica gel chromatography (hexane:ethyl acetate=5:1) to obtain a yellow solid (Compound 2a) (190 mg, 0.780 mmol, 2 stages 79%).

m.p 92.3-93.9° C., $^1$H NMR (400 MHz, $CDCl_3$) δ 9.43 (d, J=2.0 Hz, 1H), 9.03 (d, J=1.9 Hz, 1H), 4.02 (s, 3H), 3.98 (s, 3H); $^{13}$C NMR (100 MHz, $CDCl_3$) δ 169.6, 163.8, 154.8, 137.1, 134.1, 122.4, 65.6, 53.0; HRMS (ES+) calcd for $C_3H_8N_2O_5NaS$ [M+Na]$^+$ 267.0052, found 267.0042.

Example 1-2: Synthesis of Compound 2b

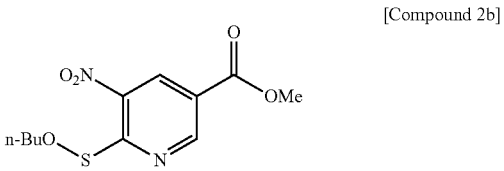

[Compound 2b]

Compound 2b (yellow solid, 72.3 mg, 2 stages 77%) was synthesized in the same manner as Compound 2a, using Compound 1 (100 mg, 0.329 mmol) and n-butanol (6 mL).

m.p 62.3-63.7° C., $^1$H NMR (400 MHz, $CDCl_3$) δ 9.42 (d, J=1.9 Hz, 1H), 9.01 (d, J=2.0 Hz, 1H), 4.08 (t, J=6.6 Hz, 2H), 4.02 (s, 3H); 1.84-1.74 (m, 2H), 1.53-1.44 (m, 2H), 0.98 (t, J=7.4 Hz, 3H); $^{13}$C NMR (100 MHz, $CDCl_3$) δ 170.1, 163.9, 154.7, 137.0, 134.0, 122.2, 78.8, 53.0, 32.8, 19.0, 13.8; HRMS (ES+) calcd for $C_{11}H_{14}N_2O_5NaS$ [M+Na]$^+$ 309.0521, found 309.0523.

Example 1-3: Synthesis of Compound 2c

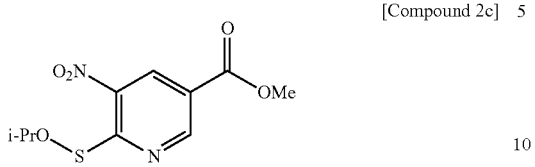

[Compound 2c]

Compound 2c (yellow solid, 25.4 mg, 2 stages 29%) was synthesized in the same manner as Compound 2a, using Compound 1 (100 mg, 0.329 mmol) and 2-propanol (6 mL).

m.p 77.6-81.1° C., $^1$H NMR (400 MHz, CDCl$_3$) δ 9.39 (s, 1H), 4.13-4.06 (m, 1H), 4.01 (s, 3H), 1.46-1.34 (m, 6H): $^{13}$C NMR (100 MHz, CDCl$_3$) δ 170.3, 163.9, 154.6, 137.2, 134.0, 122.1, 81.7, 52.9, 22.6 (2 carbons); HRMS (ES+) calcd for $C_{10}H_{12}N_2O_3NaS$ [M+Na]$^+$ 295.0365, found 295.0373.

Example 1-4: Synthesis of Compound 2d

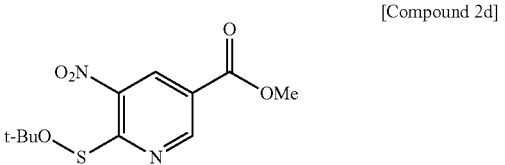 [SMILES: COC(=O)c1cnc(SOC(C)(C)C)c([N+](=O)[O-])c1]

[Compound 2d]

Compound 2d (yellow solid, 38.0 mg, 2 stages 20%) was synthesized in the same manner as Compound 2a, using Compound 1 (200 mg, 0.329 mmol) and t-butyl alcohol (3 mL).

m.p 96.6-98.9° C., $^1$H NMR (400 MHz, CDCl$_3$) δ 9.36 (d, J=2.0 Hz, 1H), 9.00 (d, J=2.0 Hz, 1H), 4.00 (s, 3H), 1.43 (s, 9H): $^{13}$C NMR (100 MHz, CDCl$_3$) δ 171.1, 163.9, 154.4, 137.0, 134.9, 122.0, 84.8, 52.9, 27.8 (3 carbons); HRMS (ES+) calcd for $C_{11}H_{15}N_2O_5S$ [M+Na]$^+$ 287.0701.

Example 1-5: Synthesis of Compound 2e

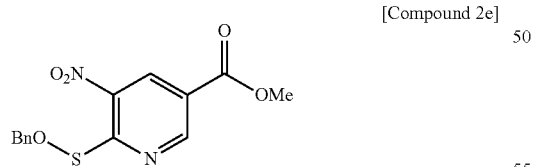

[Compound 2e]

Compound 2e (yellow solid, 84.9 mg, 2 stages 81%) was synthesized in the same manner as Compound 2a, using Compound 1 (100 mg, 0.329 mmol) and benzyl alcohol (6 mL).

m.p 120.4-122.8° C.: $^1$H NMR (400 MHz, CDCl$_3$) δ 9.46 (d, J=1.9 Hz, 1H), 9.04 (d, J=2.0 Hz, 1H), 7.52-7.48 (m, 2H), 7.44-7.37 (m, 3H), 5.07 (s 2H), 4.03 (s, 3H); $^{13}$C NMR (100 MHz, CDCl$_3$) δ 169.6, 16 0.9, 154.7, 137.2, 136.4, 134.1, 128.9 (3 carbons), 128.6 (2 carbon), 122.4, 79.9, 53.0, HRMS (ES+) calcd for $C_{14}H_{13}N_2O_5S$ [M+H]$^+$ 3210.0545, found 321.0544.

Example 1-6: Synthesis of Compound 2f

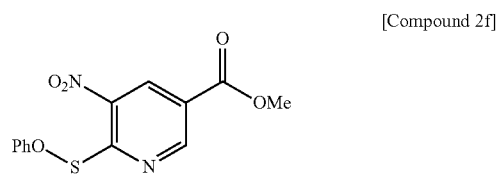 [SMILES: COC(=O)c1cnc(SOc2ccccc2)c([N+](=O)[O-])c1]

[Compound 2f]

Sulfuryl chloride (117 μL, 1.45 mmol) and pyridine (26.5 μL, 0.329 mmol) were added at room temperature to a solution of Compound 1 (200 mg, 0.657 mmol) in 1,2-dichloroethane (1.5 mL), and the mixture was stirred at the same temperature for 1 hour. The reaction solution was distilled off under reduced pressure and subjected to azeotropy with hexane. The obtained residue was used for the next reaction without purification. The obtained residue was dissolved in THF (3.3 mL), and phenol (57.8 μL, 0.657 mmol) was added in the light shielding at room temperature, N,N-diisopropylethylamine (142 μL, 0.986 mmol) was added while stirring in an ice salt bath, and the mixture was stirred at the same temperature for 2 hours. The reaction solution was distilled off under reduced pressure, and the obtained residue was diluted with chloroform, washed with 5% citric acid aqueous solution, water, and saturated brine, and dried over Na$_2$SO$_4$. After filtration, the mother liquid was distilled off under reduced pressure, and the obtained residue was purified by silica gel chromatography (chloroform) to obtain a yellow solid (Compound 2f) (116 mg, 0.379 mmol, 2 stages 58%).

m.p 163.7-165.9° C.: $^1$H NMR (400 MHz, CDCl$_3$) δ 9.33 (d, J=1.9 Hz, 1H), 9.04 (d, J=1.9 Hz, 1H), 7.33-7.27 (m, 2H), 7.25-7.22 (m, 2H), 7.09 (t, J=7.2 Hz, 1H), 4.00 (s, 3H; $^{13}$C NMR (100 MHz, CDCl$_3$) δ 167.8, 163.6, 159.0, 155.1, 137.2, 133.9, 129.4 (2 carbons), 123.8, 123.0, 117.0 (2 carbons), 53.1; HRMS (ES+) calcd for $C_{13}H_{11}N_2O_3S$ [M+H]$^+$ 307.0389, found 307.090.

Example 1-7: Synthesis of Compound 2g

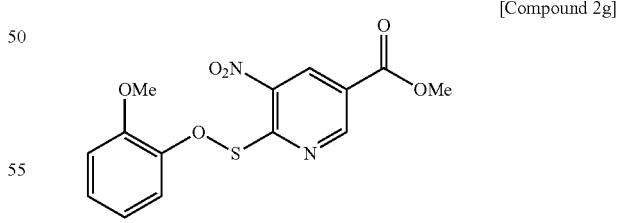

[Compound 2g]

Compound 2g (yellow viscous substance, 12.9 mg, 2 stages 12%) was synthesized in the same manner as Compound 2f, using Compound 1 (100 mg, 0.328 mmol) and o-methoxyphenol (0.328 mmol).

$^1$H NMR (400 MHz, CDCl$_3$) δ 9.39 (d, J=1.9 Hz, 1H), 9.02 (d, J=1.9 Hz, 1H), 7.35 (dd, J=8.1 and 1.5 Hz, 1H), 7.12-6.94 (m, 2H), 6.86-6.79 (m, 1H), 4.00 (s, 3H), 3.97 (s, 3H).

Example 1-8: Synthesis of Compound 2h

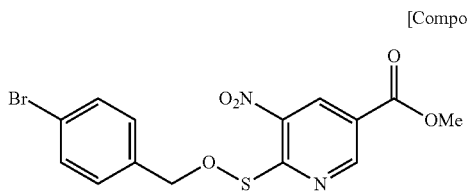

[Compound 2h]

Compound 2h (yellow solid, 65.1 mg, 2 stages 50%) was synthesized in the same manner as Compound 2f, using Compound 1 (100 mg, 0.328 mmol) and p-bromobenzyl alcohol (61.3 mg, 0.328 mmol).

$^1$H NMR (400 MHz, CDCl$_3$) δ 9.45 (d, J=1.9 Hz, 1H), 9.04 (d, J=1.9 Hz, 1H), 7.54 (d, J=8.4 Hz, 2H), 7.38 (d, J=8.4 Hz, 2H), 5.01 (s, 2H), 4.03 (s, 3H); HRMS (ES+) calcd for C$_{14}$H$_{12}$N$_2$O$_5$SBr [M+H]$^+$ 398.9650, found 398.9664.

Example 1-9: Synthesis of Compound 2i

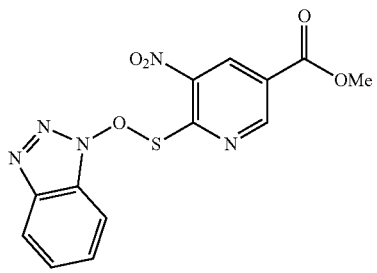

[Compound 2i]

Sulfuryl chloride (59 μL, 0.72 mmol) and pyridine (13 μL, 0.16 mmol) were added at room temperature to a solution of Compound 1 (100 mg, 0.33 mmol) in 1,2-dichloroethane (0.75 mL), and the mixture was stirred at the same temperature for 2 hours. The reaction solution was distilled off under reduced pressure and subjected to azeotropy with hexane. The obtained residue was used for the next reaction without purification. The obtained residue was dissolved in 1,2-dichloroethane (1 mL), 1-hydroxybenzotriazole (HOBt.H$_2$O, 49 mg, 0.32 mmol) and pyridine (0.1 mL, 1.29 mmol) were added in the light shielding at room temperature, and the mixture was stirred at the same temperature for 30 minutes. The reaction solution was distilled off under reduced pressure, and the obtained residue was diluted with chloroform, washed with 5% citric acid aqueous solution, water, and saturated brine, and dried over Na$_2$SO$_4$. After filtration, the mother liquid was distilled off under reduced pressure, and the obtained residue was purified by silica gel chromatography (hexane:ethyl acetate=5:1) to obtain a yellow solid (Compound 2i) (17 mg, 48.9 μmol, 2 stages 15%).

$^1$H NMR (400 MHz, CDCl$_3$) δ 9.14 (d, J=1.9 Hz, 1H) 8.81 (d, J=1.9 Hz, 1H), 8.18-8.12 (m, 1H), 7.62-7.56 (m, 1H), 7.55-7.48 (m, 2H), 3.99 (s, 3H).

Example 2

A disulfide-containing peptide was synthesized by forming a disulfide bond in the molecule of the peptide having two free thiol groups, using the above-synthesized nitrogen-containing compound according to the present invention as a selective disulfidation agent.

Example 2-1 (a): Synthesis of Oxytocin Using Compound 2a

Oxytocin (peptide 4), which is a nonapeptide (9 amino acids) having a pair of disulfide bonds (between the 1$^{st}$ and 6$^{th}$ cysteine residues from the N-terminal side) in the molecule, was synthesized by the following scheme using the above-synthesized Compound 2a as a selective disulfidation agent.

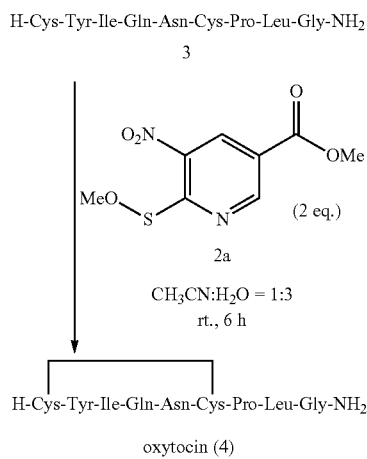

A specific method thereof is as follows.

Synthesis of H-Cys-Tyr-Ile-Gln-Asn-Cys-Pro-Leu-Gly-NH$_2$ (peptide 3)

A 20% (v/v) piperidine/dimethylformamide solution was added to Fmoc-Rink-amide resin (0.58 mmol/g, 200 mg, 0.116 mmol) and shaken at room temperature. After the reaction solution was removed by filtration, the peptide chain was elongated by the Fmoc-solid phase peptide synthesis method, using a Fmoc-amino acid derivative (3 equivalents), 1-hydroxybenzotriazole (HOBt.H$_2$O, 3 equivalents), and N,N'-diisopropylcarbodiimide (DIPCI, 3 equivalents). To the obtained H-Cys(Trt)-Tyr(t-Bu)-Ile-Gln(Trt)-Asn(Trt)-Cys(Trt)-Pro-Leu-Gly-NH-resin (331 mg), TFA:H$_2$O:triisopropylsilane:1,2-ethanedithiol (94:2.5:1.0:2.5 (volume ratio), 10 mL) was added, and the mixture was stirred at room temperature for 3 hours. The reaction solution was filtered, TFA was removed, and ether was added to precipitate the peptide. The peptide was washed twice with ether, and dried. The crude product was purified by HPLC (gradient: milliQ (0.1% TFA)/CH$_3$CN (0.1% TFA)=79:21 to 74:26 over 15 min, flow rate 5 mL/min, UV: 230 nm, column: Sunfire™ Prep C18 OBD™5 μm, 19×150 mm Column) to obtain peptide 3 (49.6 mg, 44.2 μmol, 38%).

HRMS (ES+) calcd for C$_{43}$H$_{69}$N$_{12}$O$_{12}$S$_2$[M+H]$^+$ 1009.4599, found 1009.4573.

Synthesis of Oxytocin (Peptide 4)

Compound 2a (0.31, 2 equivalents) was added to a mixed solution of peptide 3 (0.71 mg, 0.63 μmol) in acetonitrile/water (1:3 (volume ratio), 0.1 mM) at room temperature, and stirred in the light shielding at the same temperature for 6 hours. The fraction detected as the main peak was analyzed by TOF-MS to confirm the synthesis of oxytocin (peptide 4).

HRMS (ES+) calcd for $C_{42}H_{67}N_{12}O_{12}S_2$ [M+H]$^+$ 1007.4443, found 1007.4440.

Further, analysis results of the reaction system before an addition (A) of Compound 2a, after 1 hour from the addition (B), and after 6 hours from the addition (C) when peptide 4 was synthesized from peptide 3 are shown in FIG. 1, the analysis results being obtained by HPLC (gradient: milliQ (0.1% TFA)/CH$_3$CN=85:15 to 65:35 over 20 min, flow rate 1 mL/min, UV: 230 nm, column: COSMOSIL Packed Column 5C$_4$-AR-300 4.6 ID×150 mm). Further, in the drawings, * is a non-peptide peak (hereinafter, applied as the same as above). As shown in FIG. 1, after 1 hour from the addition of Compound 2a, the peak of peptide 3 almost disappeared, and the peak of the product (peptide 4) was confirmed. In addition, after 6 hours of addition, the peak of peptide 3 completely disappeared and the peak of Compound 2a also remained only slightly. Thus, it is shown that by using the nitrogen-containing compound (or a salt thereof) according to the present invention as the disulfidation reagent, it is possible to synthesize the disulfide-containing peptide by introducing the disulfide bond in the molecule of the peptide in a short time by a very simple treatment and also by a chemically stable method. In addition, the presumptive reaction mechanism into which the disulfide bond is introduced in the present Example is as follows.

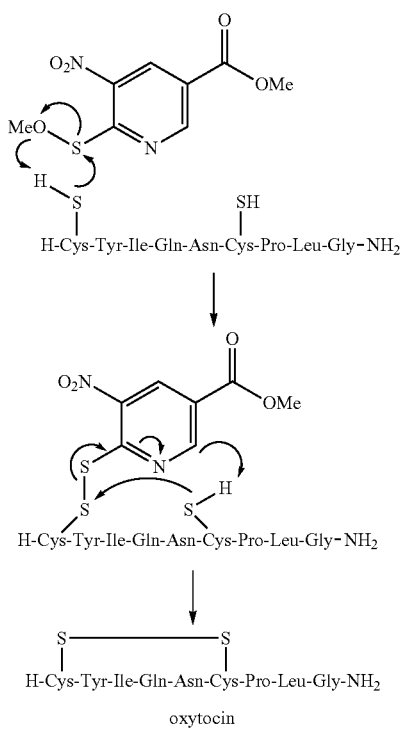

Example 2-1(b): Synthesis of Oxytocin Using Compound 2b

Oxytocin (peptide 4) was synthesized by the same method as in Example 2-1(a) above, except that Compound 2b was used as a selective disulfidation agent instead of Compound 2a. In addition, the fraction detected as the main peak was analyzed by TOF-MS in the same manner as described above to confirm the synthesis of oxytocin (peptide 4).

Example 2-1(c): Synthesis of Oxytocin Using Compound 2c

Oxytocin (peptide 4) was synthesized by the same method as in Example 2-1(a) above, except that Compound 2c was used as a selective disulfidation agent instead of Compound 2a. In addition, the fraction detected as the main peak was analyzed by TOF-MS in the same manner as described above to confirm the synthesis of oxytocin (peptide 4).

Example 2-1(d): Synthesis of Oxytocin Using Compound 2d

Oxytocin (peptide 4) was synthesized by the same method as in Example 2-1(a) above, except that Compound 2d was used as a selective disulfidation agent instead of Compound 2a. In addition, the fraction detected as the main peak was analyzed by TOF-MS in the same manner as described above to confirm the synthesis of oxytocin (peptide 4).

Here, the yield of oxytocin (Peptide 4) with respect to each of Examples 2-1(a) to 2-1(d), was measured by HPLC analysis of the reaction solution after 1 hour, 3 hours, and 6 hours from the addition of the selective disulfidation agent. Results are shown in Table 1 below.

Further, the HPLC conditions of Examples 2-1(a) to 2-1(d) are as follows. Example 2-1(a) gradient: milliQ (0.1% TFA)/CH$_3$CN=85:15 to 65:35 over 20 min, flow rate 1 mL/min, UV: 230 nm, column: COSMOSIL Packed Column 5C$_4$-AR-300 4.6 ID×150 mm, Example 2-1(b) gradient: milliQ (0.1% TFA)/CH$_3$CN=85:15 to 45:55 over 40 min, flow rate 1 mL/min, UV: 230 nm, column: COSMOSIL Packed Column 5C$_4$-AR-300 4.6 ID×150 mm, Examples 2-1(c) and 2-1(d) gradient: milliQ (0.1% TFA)/CH$_3$CN=85:15 to 55:45 over 30 min, flow rate 1 mL/min, UV: 230 nm, column: COSMOSIL Packed Column 5C$_4$-AR-300 4.6 ID×150 mm.

TABLE 1

Yield of oxytocin synthesis by Compounds 2a to 2d

| Entry | Compound | Yield of peptide 4 (%)[a] | | |
|---|---|---|---|---|
| | | 1 hour | 3 hours | 6 hours |
| 1 | 2a | 63 | 83 | 90 |
| 2 | 2b | 17 | 47 | 68 |
| 3 | 2c | 15 | 44 | 60 |
| 4 | 2d | 4 | 14 | 29 |

[a]HPLC yield of oxytocin produced in reaction solution

Example 2-2: Synthesis of Human Atrial Sodium Diuretic Peptide (Human ANP) (Peptide 6)

Human atrial sodium diuretic peptide (Human ANP) (peptide 6), which is a polypeptide (28 amino acids) having a pair of disulfide bonds (between the 7th and 23$^{rd}$ cysteine residues from the N-terminal side) in the molecule, was synthesized by the following scheme.

H-SLRRSSCFGGRMDRIGAQSGLGCNSFRY-OH

5

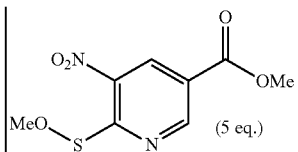

CH$_3$CN:H$_2$O = 1:3
rt., 24 h
HPLC purification
50%

H-SLRRSSCFGGRMDRIGAQSGLGCNSFRY-OH human ANP (6)

A specific method thereof is as follows.

Synthesis of H-Ser-Leu-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH (peptide 5)

The peptide chain was elongated with a Prelude® 6 channel peptide synthesizer using Fmoc-Tyr(t-Bu)-TrtA-PEG-resin (0.22 mmol/g, 182 mg, 80.0 μmol). To a part (244 mg) of the obtained H-Ser(t-Bu)-Leu-Arg(Pbf)-Arg(Pbf)-Ser(t-Bu)-Ser(t-Bu)-Cys(Trt)-Phe-Gly-Gly-Arg(Pbf)-Met-Asp(Ot-Bu)-Arg(Pbf)-Ile-Gly-Ala-Gln(Trt)-Ser(t-Bu)-Gly-Leu-Gly-Cys(Trt)-Asn(Trt)-Ser(t-Bu)-Phe-Arg(Pbf)-Tyr(t-Bu)-O-resin (710 mg), TFA:H$_2$O triisopropylsilane:1,2-ethanedithiol (94:2.5:1.0:2.5 (volume ratio), 5 mL) was added, and the mixture was stirred at room temperature for 3 hours. The reaction solution was filtered, TFA was removed, and ether was added to precipitate the peptide. The peptide was washed twice with ether, and dried. The crude product was purified by HPLC (gradient: milliQ (0.1% TFA)/CH$_3$CN (0.1% TFA)=80:20 to 67:33 over 13 min, flow rate 5 mL/min, UV: 230 nm, column: Sunfire™ Prep C18 OBD™ 5 μm, 19×150 mm Column) to obtain peptide 5 (11.3 mg, 3.01 μmol, 10%).

HRMS (ES+) calcd for C$_{127}$H$_{206}$N$_{45}$O$_{39}$S$_3$ [M+H]$^+$ 3081.4682, found 3081.4697.

Synthesis of Human Atrial Sodium Diuretic Peptide (Human ANP) (Peptide 6)

Compound 2a (0.49 mg, 2.02 μmol) was added to a mixed solution of peptide 5 (1.52 mg, 0.403 μmol) in acetonitrile/water (1:3, 403 μL), and stirred in the light shielding at room temperature for 24 hours. The reaction solution was purified by HPLC (gradient: milliQ (0.1% TFA)/CH$_3$CN (0.1% TFA)=80:20 to 67:33 over 13 min, flow rate 5 mL/min, UV: 230 nm, column: Sunfire™ Prep C18 OBD™ 5 μm, 19×150 mm Column) to obtain human atrial sodium diuretic peptide (Human ANP) (peptide 6) (0.76 mg, 2.02 μmol, 50%).

HRMS (ES+) calcd for C$_{127}$H$_{204}$N$_{39}$S$_3$ [M+H]$^+$ 3079.4525, found 3079.4573.

Further, analysis results of the reaction system before an addition (A) of Compound 2a, after 1 hour from the addition (B), after 6 hours from the addition (C), and after 24 hours from the addition (D) when peptide 6 was synthesized from peptide 5 are shown in FIG. 2, the analysis results being obtained by HPLC (gradient: milliQ (0.1% TFA)/CH$_3$CN=95:5 to 35:65 over 30 min, flow rate 1 mL/min, UV: 230 nm, column: COSMOSIL Packed Column 5C$_4$-AR-300 4.6 ID×150 mm). As shown in FIG. 2, after 1 hour from the addition of Compound 2a, the peak of peptide 5 decreased to about half and the peak of the product (peptide 6) was confirmed. In addition, after 6 hours from the addition, the peak of peptide 5 very decreased, and the peak of the product (peptide 6) increased. In addition, after 24 hours from the addition, the peak of peptide 5 completely disappeared, and the peak of Compound 2a also showed a large decrease. From the above description, it can be appreciated that the disulfidation reagent including the nitrogen-containing compound (or a salt thereof) according to the present invention can introduce the disulfide bond in the molecule, thereby synthesizing a disulfide-containing peptide even if a relatively large polypeptide of 28 amino acids is used as a raw material.

Example 2-3: Synthesis of α-conotoxin ImI (peptide 9)

By the following scheme, α-conotoxin ImI (peptide 9), which is a polypeptide (12 amino acids) having two pairs of disulfide bonds in the molecule (between the 1$^{st}$ and 10$^{th}$ cysteine residues and between the 5$^{th}$ and 11$^{th}$ cysteine residues from the N-terminal side), was synthesized.

H-Gly-Cys-Cys-Ser-Asp-Pro-Arg-Cys-Ala-Trp-Arg-Cys-NH$_2$
　　　|　　　　　　　　　　　　　　　　　　　|
　　　Acm　　　　　　　　　　　　　　　　　Acm

7

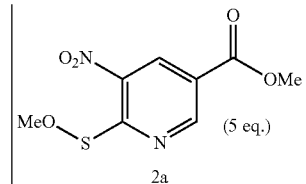

CH$_3$CN:H$_2$O = 1:3
rt., 27 h
HPLC purification
61%

H-Gly-Cys-Cys-Ser-Asp-Pro-Arg-Cys-Ala-Trp-Arg-Cys-NH$_2$
　　　|　　　　　　　　　　　　　　　　　　　|
　　　Acm　　　　　　　　　　　　　　　　　Acm

8

H-Gly-Cys-Cys-Ser-Asp-Pro-Arg-Cys-Ala-Trp-Arg-Cys-NH$_2$
　　　|　　　　　　　　　　　　　　　　　　　|
　　　Acm　　　　　　　　　　　　　　　　　Acm

8

I$_2$ (5 eq.)
CH$_3$CN:H$_2$O = 5:1
rt., 1 h
HPLC purification
46%

-continued

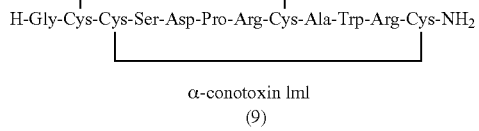

α-conotoxin ImI
(9)

A specific method thereof is as follows.

Synthesis of H-Gly-Cys-Cys(Acm)-Ser-Asp-Pro-Arg-Cys-Ala-Trp-Arg-Cys(Acm)-NH$_2$ (Peptide 7)

The peptide chain was elongated with a Prelude® 6 channel peptide synthesizer using Fmoc-SAL-amide resin (0.54 mmol/g, 148 mg, 80.0 µmol). To the obtained H-Gly-Cys(Trt)-Cys(Acm)-Ser(t-Bu)-Asp(t-Bu)-Pro-Arg(Pbf)-Cys(Trt)-Ala-Trp(Boc)-Arg(Pbf)-Cys(Acm)-NH-resin (362 mg), TFA:H$_2$O: triisopropylsilane:1,2-ethanediol (94:2.5:1.0:2.5 (volume ratio), 5 mL) was added, and the mixture was stirred at room temperature for 3 hours. The reaction solution was filtered, TFA was removed, and ether was added to precipitate the peptide. The peptide was washed twice with ether, and dried. The crude product was purified by HPLC (gradient: milliQ (0.1% TFA)/CH$_3$CN (0.1% TFA)=85:15 to 72:28 over 13 min, flow rate 5 mL/min, UV: 230 nm, column: Sunfire™ Prep C18 OBD™ 5 µm, 19×150 mm Column) to obtain peptide 7 (39.9 mg, 21.7 µmol, 27%).

HRMS (ES+) calcd for C$_{58}$H$_{93}$N$_{22}$O$_{17}$S$_4$ [M+H]$^+$ 1497.5972, found 1497.5964.

In addition, the thiol groups of the 3$^{rd}$ and 12$^{th}$ cysteine residues from the N-terminal side of the peptide 7 were protected with N-(acetyl) aminomethyl groups (Acm groups), and these Acm groups can be selectively deprotected by iodine oxidation.

Synthesis of Peptide 8 (a Peptide in which a Disulfide Bond is Formed Between the 2$^{nd}$ and 8$^{th}$ Cysteine Residues from the N-Terminal Side of Peptide 7)

A mixed solution of Compound 2a (0.33 mg, 1.36 µmol) in acetonitrile/water (1:3 (volume ratio), 3.34 mL) was added to the peptide 7 (6.14 mg, 3.34 µmol) at room temperature, and the mixture was stirred in the light shielding at the same temperature for 27 hours. The reaction solution was purified by HPLC (gradient:milliQ (0.1% TFA)/CH$_3$CN (0.1% TFA)=85:15 to 77:23 over 16 min, flow rate 5 mL/min, UV: 230 nm, column: Sunfire™ Prep C18 OBD™ 5 µm, 19×150 mm Column) to obtain peptide 8 (3.75 mg, 2.04 µmol, 61%).

HRMS (ES+) calcd for C$_{58}$H$_{91}$N$_{22}$O$_{17}$S$_4$[M+H]$^+$ 1495.5815, found 1495.5814.

Further, analysis results of the reaction system before an addition of Compound 2a (A), after 4 hours from the addition (B), after 9 hours from the addition (C), and after 27 hours from the addition (D) when peptide 8 was synthesized from peptide 7 are shown in FIG. 3, the analysis results being obtained by HPLC (gradient:milliQ (0.1% TFA)/CH$_3$CN=95:5 to 35:65 over 30 min, flow rate 1 mL/min, UV: 230 nm, column: COSMOSIL Packed Column 5C$_4$-AR-300 4.6 ID×150 mm). As shown in FIG. 3, after 4 hours from the addition of Compound 2a, the peak of peptide 7 decreased to about half and the peak of the product (peptide 8) was confirmed. In addition, after 9 hour from the addition, the peak of peptide 7 very decreased, and the peak of the product (peptide 8) increased. In addition, after 27 hours from the addition, the peak of peptide 7 completely disappeared, and the peak of Compound 2a also showed a large decrease. Here, the analysis results of the sample after purifying the reaction solution by HPLC (gradient: milliQ (0.1% TFA)/CH$_3$CN=95:5 to 35:65 over 30 min, flow rate 1 mL/min, UV: 230 nm, column: COSMOSIL Packed Column 5C$_4$-AR-300 4.6 ID×150 mm) are shown in (E) of FIG. 3. As can be appreciated from the results, the peak of the product obtained by the purification was consistent with the peak of peptide 8 in view of the retention time.

Synthesis of α-conotoxin ImI (peptide 9)

Iodine (I$_2$) (2.03 mg, 8.00 µmol) was added to a mixed solution of peptide 8 (2.94 mg, 1.60 μmol) in acetonitrile/water (5:1 (volume ratio), 1.60 mL) at room temperature, and stirred in the light shielding at the same temperature for 1 hour. Thus, the disulfide bond was formed between the corresponding two thiol groups while simultaneously performing the deprotection of the Acm groups at two positions in peptide 7 (iodine oxidation method). To the reaction solution, 1 M aqueous sodium ascorbate solution (50 μL) was added, and the mixture was purified by HPLC (gradient: milliQ (0.1% TFA)/$CH_3CN$ (0.1% TFA)=85:15 to 77:23 over 16 min, flow rate 5 mL/min, UV: 230 nm, column: Sunfire™ Prep C18 OBD™ 5 μm, 19×150 mm Column) to obtain α-conotoxin ImI (peptide 9) (1.25 mg, 0.738 μmol, 46%).

HRMS (ES+) calcd for $C_{52}H_{79}N_{20}O_{15}S_4$ $[M+H]^+$ 1351.4917, found 1351.4915.

Further, analysis results of the reaction system before an addition of iodine (A), after 2 minutes from the addition (B), after 1 hour from the addition (C), and after HPLC purification (D) when peptide 9 was synthesized from peptide 8 are shown in FIG. 4, the analysis results being obtained by HPLC (gradient: milliQ (0.1% TFA)/$CH_3CN$=95:5 to 35:65 over 30 min, flow rate 1 mL/min, UV: 230 nm, column: COSMOSIL Packed Column $5C_4$-AR-300 4.6 ID×150 mm). As shown in FIG. 4, after 2 minutes from the addition of iodine, the peak of peptide 8 greatly decreased and the peak of the product (peptide 9) increased. In addition, after 1 hour from the addition, the peak of peptide 8 completely disappeared, and only the peak of the product (peptide 9) was confirmed. As can be appreciated from the HPLC analysis results ((D) of FIG. 4) after purifying the reaction solution by HPLC, the peak of the product obtained by the purification was consistent with the peak of peptide 9 in view of the retention time. In addition, FIG. 5 shows analysis results of (A) α-conotoxin ImI (peptide 9) synthesized in the above Example, (B) a commercially available standard sample α-conotoxin ImI (purchased from Peptide Institute, Inc.), and (C) a mixed sample thereof, respectively, obtained by HPLC (gradient: milliQ (0.1% TFA)/$CH_3CN$=95:5 to 35:65 over 30 min, flow rate 1 mL/min, UV: 230 nm, column: COSMOSIL Packed Column $5C_4$-AR-300 4.6 ID×150 mm). As can be appreciated from these results, the retention time of the α-conotoxin ImI (peptide 9) synthesized by the above Example was consistent with that of the commercially available one. As described above, it is possible to synthesize a peptide having two disulfide bonds in a molecule, such as α-conotoxin ImI, at a high purity, and thus it may be appreciated that the method for producing the disulfide-containing peptide using the nitrogen-containing compound (or a salt thereof) according to the present invention as a disulfidation reagent provides a very strong synthesis means.

Example 3

A disulfide-containing peptide was synthesized by forming a disulfide bond in the molecule of a peptide having two free thiol groups using the above-synthesized nitrogen-containing compound according to the present invention which is solidified on the polymer carrier, as a selective disulfidation agent.

Example 3-1: Synthesis of Solid Phase Disulfidation Reagent (Compound 11)

A nitrogen-containing compound (Compound 11), in which R in Chemical Formula 1 is a polymer carrier (polyethylene glycol crosslinked product), was synthesized by the following scheme.

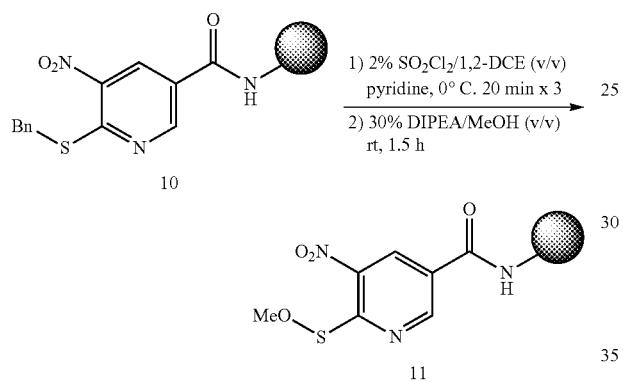

Synthesis of Compound 10

First, Compound 10 formed by solidifying a nitrogen-containing compound having the above chemical structure was synthesized on a surface of an aminomethyl-ChemMatrix® resin, which is a polymer carrier (product of Sigma-Aldrich, a large number of aminomethyl groups present on the surface, a functional group substitution ratio of 0.70 mmol/g), as described in the pamphlet of International Publication No. 2015/050199 (same as Compound 6 in Example of the pamphlet of International Publication no. 2015/050199).

Synthesis of Compound 11

Subsequently, a mixed solution of 2% (w/v) sulfuryl chloride/1,2-dichloroethane (1.25 mL) and pyridine (6.35 µL, 78.6 µmol) was added to Compound 10 (26.6 mg, 15.7 µmol) under ice-cooling, and the mixture was stirred at the same temperature for 20 minutes. After the reaction solution was removed, the mixed solvent was added under ice cooling, and stirred at the same temperature for 20 minutes. This operation was performed once again. The reaction solution was removed by filtration, and then the resin was washed five times with ice-cold dichloromethane. A mixed solvent of 30% (w/v) DIPEA/methanol (800 µL) was added to the obtained resin at room temperature, and the mixture was stirred for 1.5 hours. The reaction solution was removed by filtration, and then resin was washed five times with dichloromethane and five times with methanol. After this operation was performed twice more, the resin was dried (22.0 mg). Thus, Compound 11 was obtained.

Example 3-2: Synthesis of Oxytocin (Peptide 4) Using Solid Phase Disulfidation Reagent (Compound 11)

Oxytocin (peptide 4) was synthesized from peptide 3 in the same manner as in Example 2-1(a), using Compound 11, which is a solid phase disulfidation reagent, by the following scheme.

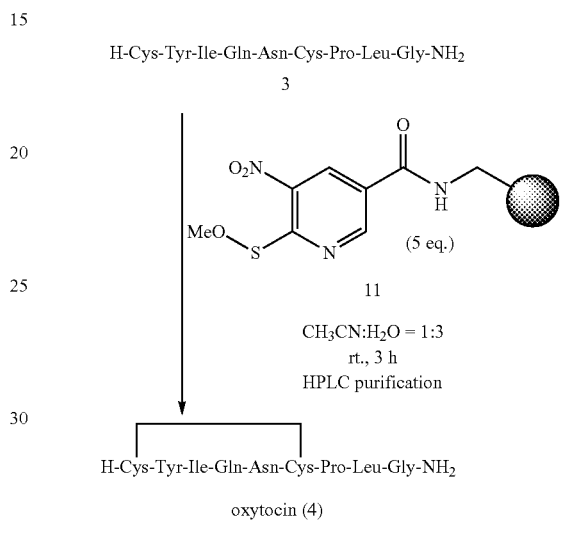

A specific method thereof is as follows.

Synthesis of Oxytocin (Peptide 4) Using Compound 11

A mixed solution of peptide 3 (1.56 mg, 1.39 µmol) in acetonitrile/water (1:3 (volume ratio), 1.39 mL) was added at room temperature to the solid phase disulfidation reagent (Compound 11) (11.8 mg, 6.94 µmol), and the mixture was stirred in the light shielding at the same temperature for 3 hours. The reaction solution was filtered and purified by HPLC (gradient: milliQ (0.1% TFA)/CH$_3$CN (0.1% TFA) =79:21 to 74:26 over 15 min, flow rate 6 mL/min, UV: 230 nm, column: Sunfire™ Prep C18 OBD™ 5 µm, 19×150 mm Column) to obtain oxytocin (peptide 4) (0.55 mg, 0.491 µmol, 35%).

In addition, analysis results of the reaction system within 3 minutes after the start of the reaction (A), 1 hour after the start of the reaction (B) and 3 hours after the start of the reaction (C) when peptide 4 was synthesized from peptide 3 using the solid phase disulfidation reagent (Compound 11) are shown in FIG. 6, the analysis results being obtained by HPLC (gradient: milliQ (0.1% TFA)/CH$_3$CN=85:15 to 65:35 over 20 min, flow rate 1 mL/min, UV: 230 nm, column: CCSMOSIL Packed Column 5C4-AR-300 4.6 ID×150 mm). As shown in FIG. 6, the peak of peptide 4 was confirmed within 3 minutes from the start of the reaction. In addition, after 1 hour from the start of the reaction, the peak of peptide 3 very decreased and the peak of the product (peptide 4) increased. In addition, after 3 hours of addition, the peak of peptide 3 completely disappeared. In addition, since the disulfidation reagent used in the present Example is a solid phase reagent, the reagent was recovered by filtration of the reaction solution, and does not appear as a peak in the HPLC chart. As described above, by making the disulfidation reagent into the form of a solid phase reagent composed of the nitrogen-containing compound in the form of being solidified on the polymer carrier, it is possible to produce a disulfide-containing peptide at a high yield in a very short time. In addition, it is possible to separate the product from the disulfidation reagent only by a simple operation called filtration. Therefore, the disulfidation reagent according to the present invention, particularly in the form of a solid phase reagent, can be said to be the invention having a very high advantage in the technical field of organic synthesis (in particular, peptide synthesis).

Example 4

As examples of the compound of the present invention, synthesis examples of the compounds 16a to 16j are shown below.

Compounds 16a to 16j were synthesized by the following scheme.

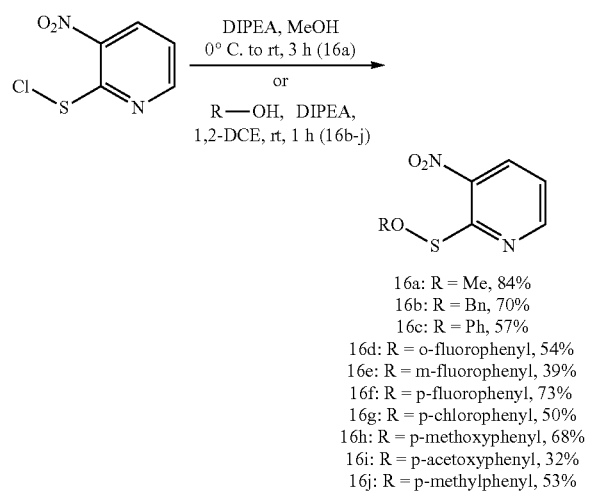

16a: R = Me, 84%
16b: R = Bn, 70%
16c: R = Ph, 57%
16d: R = o-fluorophenyl, 54%
16e: R = m-fluorophenyl, 39%
16f: R = p-fluorophenyl, 73%
16g: R = p-chlorophenyl, 50%
16h: R = p-methoxyphenyl, 68%
16i: R = p-acetoxyphenyl, 32%
16j: R = p-methylphenyl, 53%

A specific method thereof is as follows.

Example 4-1: Synthesis of Compound 16a

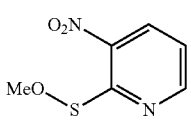

[Compound 16a]

N,N-diisopropylethylamine (2.72 mL, 18.9 mmol) was added to a solution of Npys-Cl (2.4 g, 12.6 mmol) in methanol (150 mL) under stirring while ice-cooling, and the mixture was stirred at room temperature for 3 hours. The reaction solution was distilled off under reduced pressure, and the obtained residue was diluted with chloroform, washed with 10% citric acid aqueous solution, water, and saturated brine, and dried over $Na_2SO_4$. After filtration, the mother liquid was distilled off under reduced pressure, and the obtained residue was purified by silica gel chromatography (hexane:ethyl acetate=5:1) to obtain a yellow solid (Compound 16a) (1.96 g, 10.5 mmol, 84%).

$^1$H NMR (400 MHz, $CDCl_3$) δ 8.93 (d, J=1.6 and 4.5 Hz, 1H), 8.52 (dd, J=1.6 and 8.3 Hz, 1H), 7.33-7.27 (m, 1H), 3.96 (s, 3H).

Example 4-2: Synthesis of Compound 16b

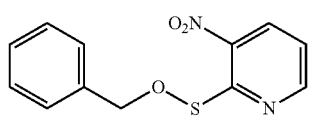

[Compound 16b]

Benzyl alcohol (28.4 mg, 0.26 mmol) and N,N-diisopropylethylamine (174 µL, 1.04 mmol) were added to a solution of Npys-Cl (50 mg, 0.26 mmol) in 1,2-dichloroethane (0.8 mL), and the mixture was stirred at the same temperature for 1 hour. The reaction solution was distilled off under reduced pressure, and the obtained residue was diluted with chloroform, washed with 5% citric acid aqueous solution, water, and saturated brine, and dried over $Na_2SO_4$. After filtration, the mother liquid was distilled off under reduced pressure, and the obtained residue was purified by silica gel chromatography (hexane:ethyl acetate=5:1) to obtain a yellow solid (Compound 16b) (48.2 mg, 70%).

$^1$H NMR (400 MHz, $CDCl_3$) δ 8.99-8.91 (m, 1H), 8.57-8.48 (m, 1H), 7.55-7.45 (m, 2H), 7.45-7.35 (m, 3H), 7.35-7.28 (m, 1H), 5.07 (s, 2H).

Example 4-3: Synthesis of Compound 16c

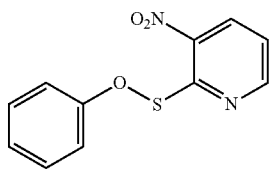

[Compound 16c]

Compound 16c (yellow solid, 37 mg, 57%) was synthesized in the same manner as Compound 16b by using Npys-Cl (50 mg, 0.26 mmol), phenol (29.6 mg, 0.31 mmol), and N,N-diisopropylethylamine (174 µL, 1.04 mmol).

$^1$H NMR (400 MHz, $CDCl_3$) δ 8.92 (d, J=4.5 Hz, 1H), 8.53 (d, J=8.3 Hz, 1H), 7.34-7.22 (m, 5H), 7.08 (t, J=7.2 Hz, 1H).

Example 4-4: Synthesis of Compound 16d

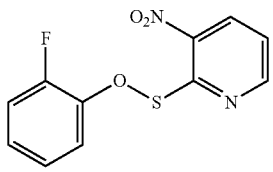

[Compound 16d]

Compound 16d (yellow solid, 38 mg, 54%) was synthesized in the same manner as compound 16b by using Npys-Cl (50 mg, 0.26 mmol), 2-fluorophenol (29.0 µL, 0.314 mmol), and N,N-diisopropylethylamine (174 µL, 1.04 mmol).

$^1$H NMR (400 MHz, CDCl$_3$) δ 8.87 (d, J=4.5 Hz, 1H), 8.53 (d, J=8.3 Hz, 1H), 7.40-7.30 (m, 2H), 7.18-7.09 (m, 1H), 7.06-6.97 (m, 2H).

Example 4-5: Synthesis of Compound 16e

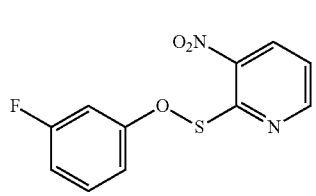

[Compound 16e]

Compound 16e (yellow solid, 27 mg, 39%) was synthesized in the same manner as Compound 16b by using Npys-Cl (50 mg, 0.26 mmol), 2-fluorophenol (28.5 µL, 0.314 mmol), and N,N-diisopropylethylamine (174 µL, 1.04 mmol).

$^1$H NMR (400 MHz, CDCl$_3$) δ 8.86-8.78 (m, 1H), 8.58-8.50 (m, 1H), 7.37-7.30 m, 1H), 7.30-7.19 (m, 1H), 7.07-7.04 (m, 1H), 7.04-6.92 (m, 1H), 6.83-6.74 (m, 1H).

Example 4-6: Synthesis of Compound 16f

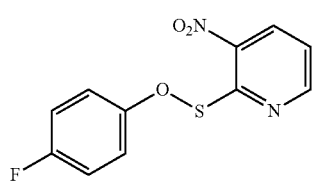

[Compound 16f]

Compound 16f (yellow solid, 51 mg, 73%) was synthesized in the same manner as Compound 16b by using Npys-Cl (50 mg, 0.26 mmol), 4-fluorophenol (35.3 mg, 0.314 mmol), and N,N-diisopropylethylamine (174 µL, 1.04 mmol).

$^1$H NMR (400 MHz, CDCl$_3$) δ 8.84 (dd, J=1.6 and 4.6 Hz, 1H), 8.54 (dd, J=1.6 and 8.4 Hz, 1H), 7.37-7.31 (m, 1H), 7.23-7.17 (m, 2H), 7.01-6.93 (m, 2H).

Example 4-7: Synthesis of Compound 16g

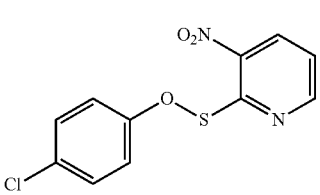

[Compound 16g]

Compound 16g (yellow solid, 37 mg, 50%) was synthesized in the same manner as Compound 16b by using Npys-Cl (50 mg, 0.26 mmol), 4-chlorophenol (25.8 µL, 0.26 mmol), and N,N-diisopropylethylamine (174 µL, 1.04 mmol).

$^1$H NMR (400 MHz, CDCl$_3$) δ 8.81 (dd, J=1.6 and 4.6 Hz, 1H), 8.54 (dd, J=1.6 and 8.3 Hz, 1H), 7.37-7.30 (m, 1H), 7.25-7.15 (m, 4H).

Example 4-8: Synthesis of Compound 16h

[Compound 16h]

Compound 16h (yellow solid, 50 mg, 68%) was synthesized in the same manner as Compound 16b by using Npys-Cl (50 mg, 0.26 mmol), 4-methoxyphenol (32.6 mg, 0.26 mmol), and N,N-diisopropylethylamine (174 µL, 1.04 mmol).

$^1$H NMR (400 MHz, CDCl$_3$) δ 8.86 (dd, J=4.5 Hz, 1H), 8.53 (d, J=8.3 Hz, 1H), 7.35-7.28 (m, 1H), 7.22-7.16 (m, 2H), 6.86-6.76 (m, 2H), 3.77 (s, 3H).

Example 4-9: Synthesis of Compound 16i

[Compound 16i]

Compound 16i (yellow solid, 26 mg, 32%) was synthesized in the same manner as Compound 16b by using Npys-Cl (50 mg, 0.26 mmol), 4-hydroxyphenylacetate (39.9 mg, 0.26 mmol), and N,N-diisopropylethylamine (174 µL, 1.04 mmol).

$^1$H NMR (400 MHz, CDCl$_3$) δ 8.83 (dd, J=1.6 and 4.5 Hz, 1H), 8.53 (dd, J=1.6 and 8.3 Hz, 1H), 7.36-7.29 (m, 1H), 7.26-7.21 (m, 2H), 7.02-6.96 (m, 2H), 2.28 (s, 3H).

Example 4-10: Synthesis of Compound 16j

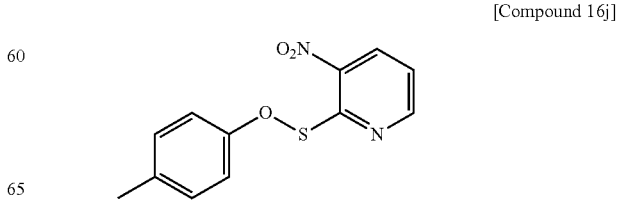

[Compound 16j]

Compound 16j (yellow solid, 36.3 mg, 53%) was synthesized in the same manner as Compound 16b by using Npys-Cl (50 mg, 0.26 mmol), p-cresol (27.3 μL, 0.26 mmol), and N,N-diisopropylethylamine (174 μL, 1.04 mmol).

$^{1}$H NMR (400 MHz, CDCl$_3$) δ 8.83 (dd, J=1.6 and 4.5 Hz, 1H), 8.52 (dd, J=1.6 and 8.4 Hz, 1H), 7.34-7.27 (m, 1H), 7.17-7.05 (m, 4H), 2.30 (m, 2H).

Example 5

Synthesis of Oxytocin Using Compound 16a

Oxytocin (peptide 4), which is a nonapeptide (9 amino acids) having a pair of disulfide bonds (between the 1$^{st}$ and 6$^{th}$ cysteine residues from the N-terminal side) in the molecule, was synthesized by the following scheme using the above-synthesized Compound 16a as a selective disulfidation agent.

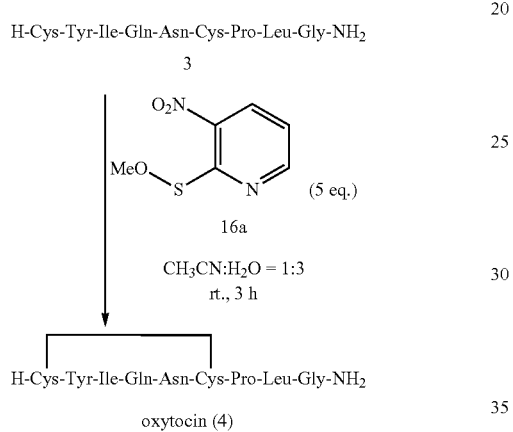

A specific method thereof is as follows.

Figure 7:
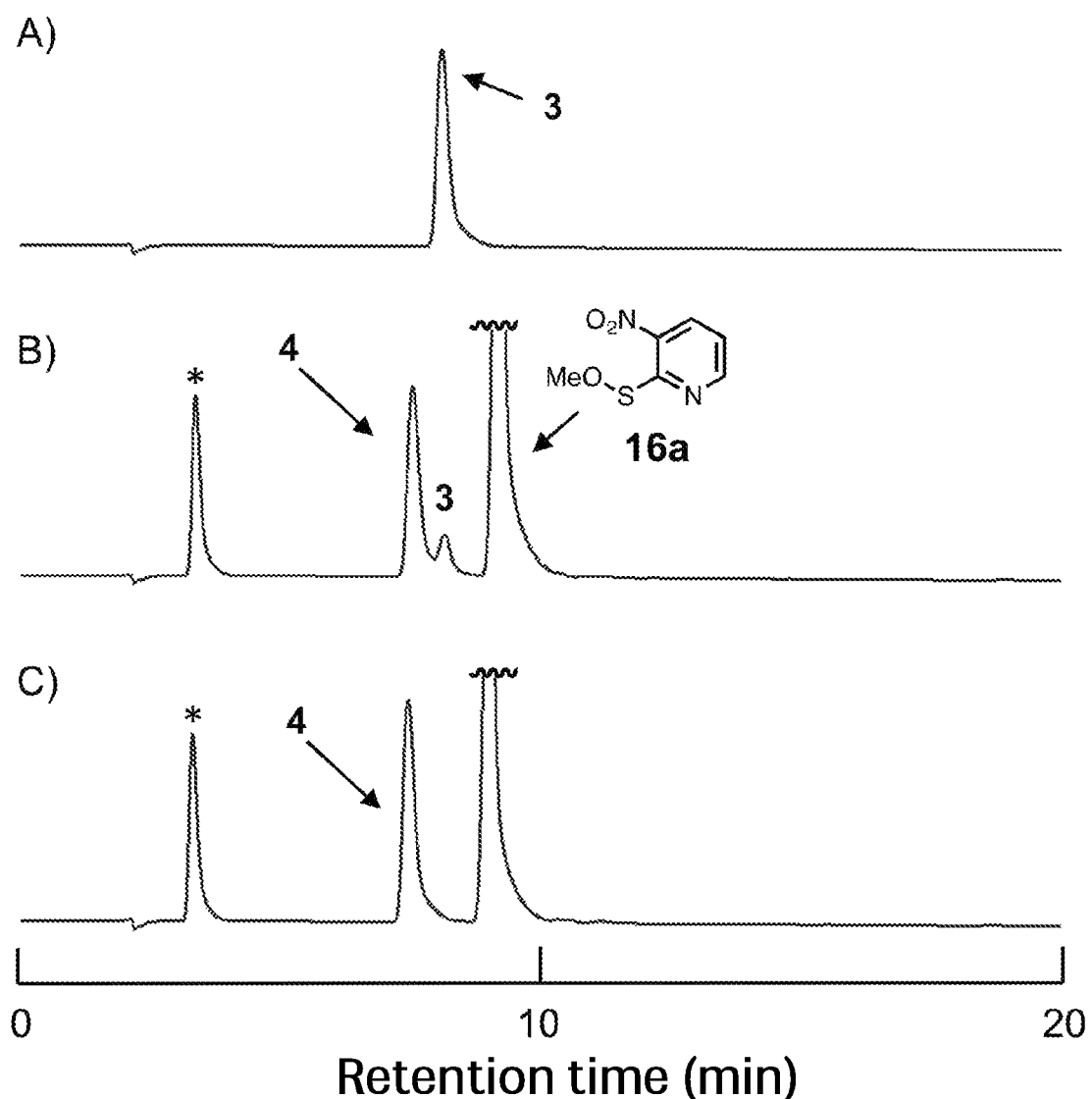
FIG. 7 is a chart showing HPLC analysis results of the reaction system before an addition of Compound 16a (A), after 1 hour from the addition (B), and after 3 hours from the addition (C) when peptide 4 is synthesized from peptide 3 in Example 5 described below.

Compound 16a (0.947 mg, 5.09 μmol) was added to a mixed solution of peptide 3 in acetonitrile/water (1:3 (volume ratio), 1 mM, 8.94 mL) at room temperature, and the mixture was stirred in the light shielding at the same temperature for 3 hours. The synthesis of oxytocin (peptide 4) was confirmed by HPLC analysis. Further, analysis results of the reaction system before an addition of Compound 16a (A), after 1 hour from the addition (B), and after 3 hours from the addition (C) when peptide 4 was synthesized from peptide 3 are shown in FIG. 7, the analysis results being obtained by HPLC (gradient: milliQ (0.1% TFA)/CH$_3$CN=85:15 to 65:35 over 20 min, flow rate 1 mL/min, UV: 230 nm, column: COSMOSIL Packed Column 5C$_4$-AR-300 4.6 ID×150 mm). As shown in FIG. 7, after 1 hour from the addition of Compound 16a, the peak of peptide 3 almost disappeared, and the peak of the product (peptide 4) was confirmed. In addition, after 3 hours of addition, the peak of peptide 3 completely disappeared. Thus, it is shown that by using the disulfidation reagent including a nitrogen-containing compound having no ester structure (or a salt thereof), likewise, it is possible to synthesize the disulfide-containing peptide by introducing the disulfide bond in the molecule of the peptide in a short time and also by a chemically stable method.

Example 6

The disulfide-containing peptide was synthesized by forming a disulfide bond between two free thiol groups of the peptide supported on a resin, using the above-synthesized nitrogen-containing compound according to the present invention as a selective disulfidation agent.

Formation of Disulfide Bond on Resin Using Compound 16a

By the following scheme, the protecting group (tert-butylthio (—S—C(CH$_3$)$_3$) group) of the side chain (—SH group) of the 1$^{st}$ and 6$^{th}$ cysteines from the N-terminal side of the oxytocin-resin 17 obtained by peptide solid phase synthesis was deprotected to form a peptide-resin 18, then the above-synthesized Compound 16a as the selective disulfidation agent was used to construct a disulfide bond on the resin, and oxytocin (peptide 4) was synthesized by deresination and deprotection of the protecting group.

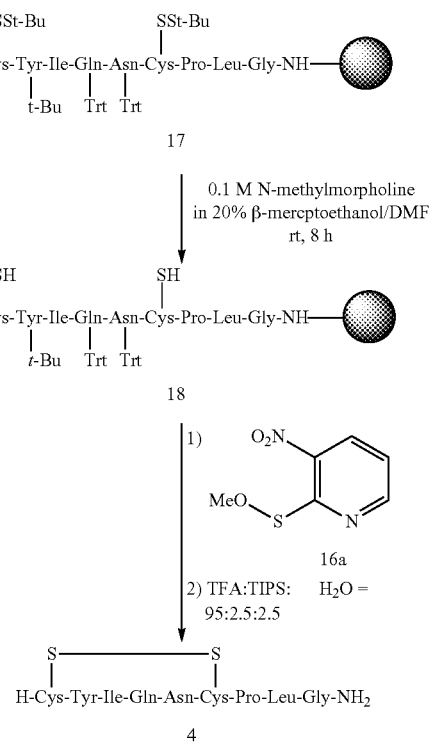

Synthesis of Oxytocin-Resin 17

The peptide chain was elongated with a Prelude® 6 channel peptide synthesizer using Fmoc-SAL-amide resin (0.56 mmol/g, 71.4 mg, 40.0 μmol) to obtain H-Cys(St-Bu)-Tyr(t-Bu)-Ile-Gln(Trt)-Asn(Trt)-Cys(St-Bu)-Pro-Leu-Gly-NH-resin (120 mg).

Synthesis of (Oxytocin (Peptide 4)

A 20% (v/v) β-mercaptoethanol/DMF mixed solution (final concentration of N-methylmorpholine 0.1 M, 1 mL) of N-methylmorpholine was added at room temperature to oxytocin-resin 17 (6.9 mg, 3.86 μmol), stirred for 8 hours, and a tert-butylthio group at the cysteine side chain was deprotected to obtain a peptide-resin 18. After the resin was washed with DMF five times, DMF (386 μL) solution of Compound 16a (1.44 mg, 7.73 μmol) was added at room temperature, and the mixture was stirred for 1 hour. After stirring, the resin was washed five times with DMF, methanol and ether, respectively, and dried. TFA:H$_2$O:triisopropylsilane:(95:2.5:2.5 (volume ratio), 1 mL) was added to the obtained resin, and the mixture was stirred at room temperature for 1 hour. The reaction solution was filtered, TFA was removed, and ether was added to precipitate the peptide. The peptide was washed twice with ether, and dried. The crude product was analyzed by HPLC to confirm the synthesis of oxytocin (peptide 4).

Figure 8:
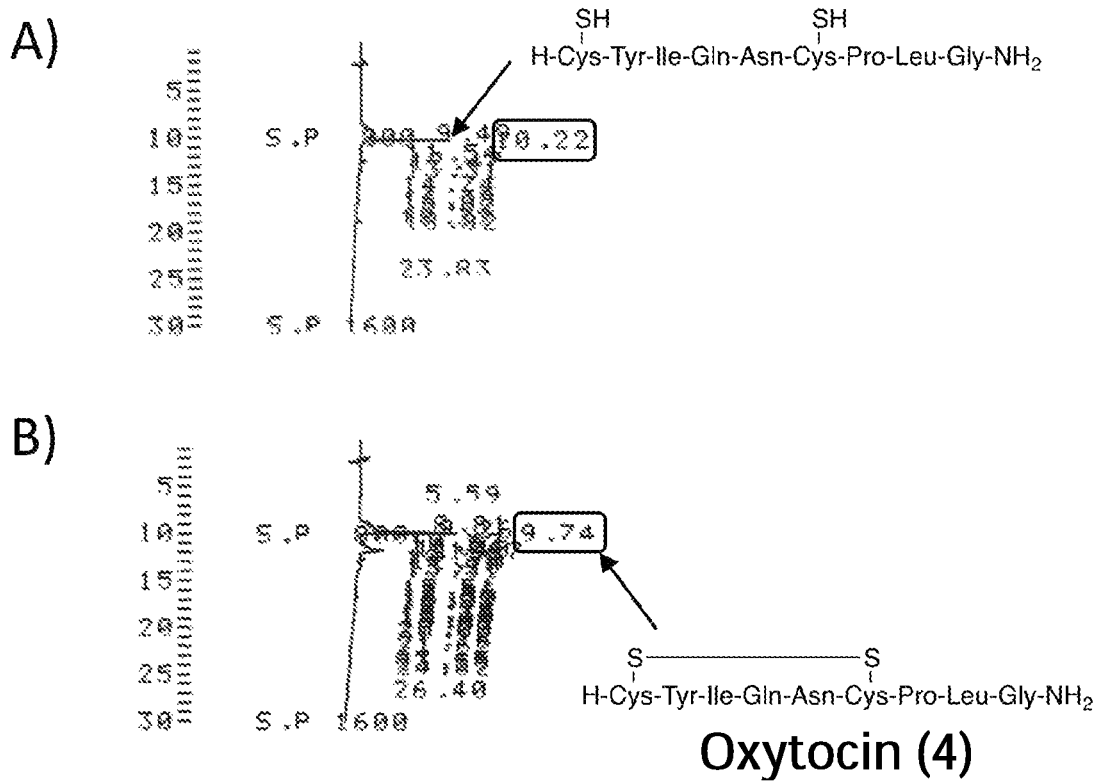
FIG. 8 shows HPLC of a crude product (B) obtained when oxytocin (peptide 4) is synthesized from oxytocin-resin 17 that is obtained by peptide solid phase synthesis in Example 6 described below.

In addition, the peptide-resin 18 was subjected to deresination, the obtained crude product (A) and Compound 16a were added thereto, and the mixture was subjected to deresination to obtain a crude product (B). The obtained crude products (A) and (B) was analyzed by HPLC (gradient: milliQ (0.1% TFA)/CH$_3$CN=85:15 to 55:45 over 30 min, flow rate 0.9 mL/min, UV: 230 nm, column: Sun Fire C18 5 µm 4.6×150 mm column), and the HPLC analysis results of the obtained crude products (A) and (B) are shown in FIG. 8. As shown in FIG. 8, a peak of the product (peptide 4) was confirmed by treating the peptide-resin 18 with Compound 16a. Thus, it is shown that the selective disulfidation reagent including the nitrogen-containing compound (or a salt thereof) forms the disulfide bond between two free thiol groups of a peptide supported on the resin, thereby making it possible to synthesize the disulfide-containing peptide.

Example 7

(Evaluation of Stability of Compound 2a)

Figure 9:
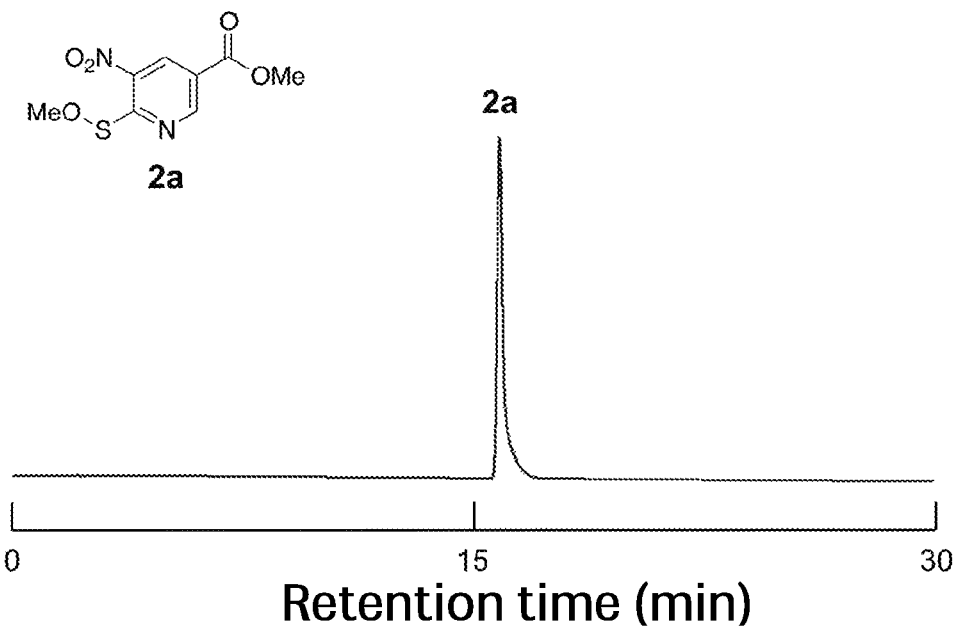
FIG. 9 is a chart showing HPLC analysis results when evaluating stability of Compound 2a in Example 7 described below.
Figure 10:
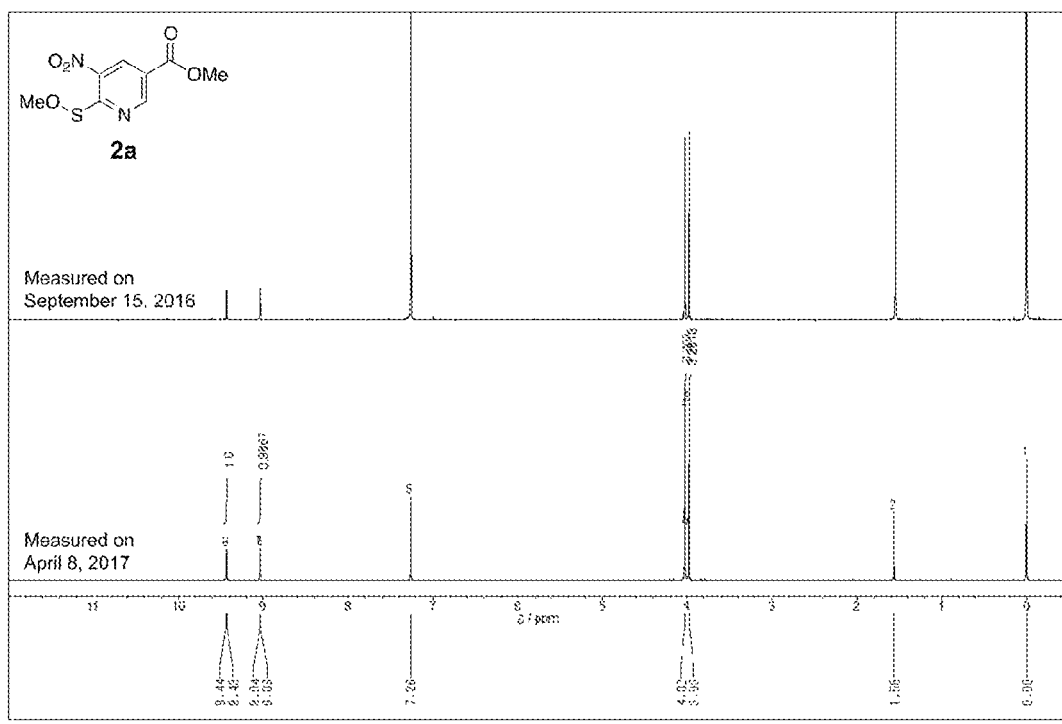
FIG. 10 is a chart showing ¹H NMR analysis results when evaluating stability of Compound 2a in Example 7 described below.

The stability of the above-synthesized nitrogen-containing Compound 2a synthesized according to the present invention was evaluated by HPLC analysis and NMR measurement. As a result, it was confirmed that Compound 2a was stable at room temperature for at least 6 months without any special treatment. Here, charts each showing HPLC analysis results (gradient: milliQ (0.1% TFA)/CH$_3$CN=95:5 to 35:65 over 30 min, flow rate 1 mL/min, UV: 230 nm, column: COSMOSIL Packed Column 5C$_4$-AR-300 4.6 ID×150 mm) and $^1$H NMR analysis results of Compound 2a over 6 months after storage at room temperature are shown in FIGS. 9 and 10.

Example 8

(Confirmation of Presence or Absence of Side Reaction by Compound 2a)

As a side reaction of iodine oxidation, iodination reaction with respect to side chains of tryptophan, tyrosine, and histidine has been reported (B. Kamber, et al., Helv. Chim. Acta. 1980, 899-915). Thus, the presence or absence of the side reaction by Compound 2a, which is the nitrogen-containing compound of the present invention, was confirmed in the same manner as in the above paper. In other words, as shown in the following scheme, Compound 2a (3 equivalents) was added to the methanol/water or DMF solution of three kinds of derivatives of tryptophan, tyrosine, and histidine (Cbz-Trp-NH$_2$, Cbz-Tyr-OMe, Cbz-Val-His-OMe) at room temperature, and stirred at the same temperature for 24 hours. As a result, it was shown that reactions of these amino acid derivatives with Compound 2a did not proceed at all, and thus there were no side reactions.

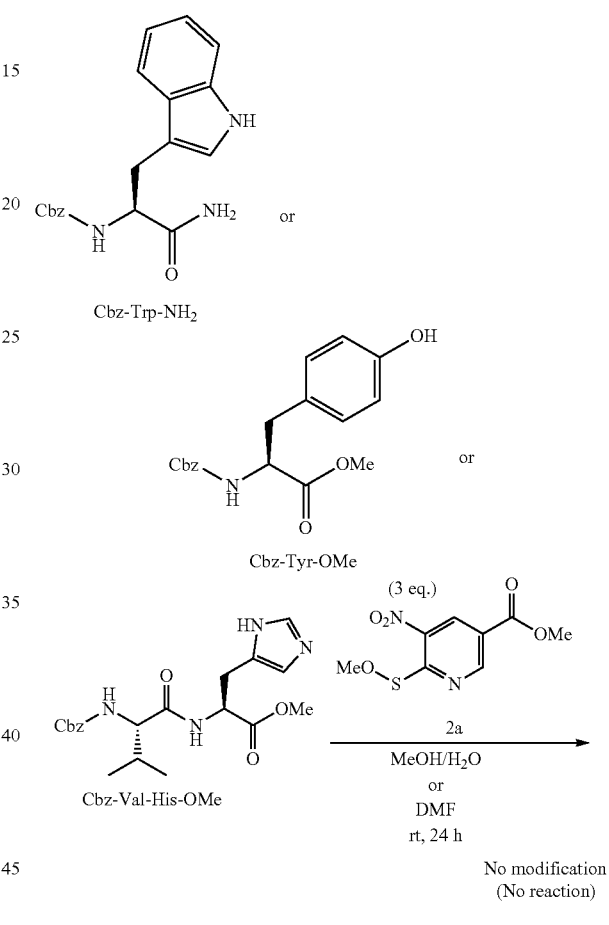

The present application is based on Japanese Patent Application No. 2016-101812 filed on May 20, 2016, the contents of which are incorporated by reference in their entirety.

The invention claimed is:

1. A nitrogen-containing compound represented by Chemical Formula 1 below or a salt thereof:

Chemical Formula 1

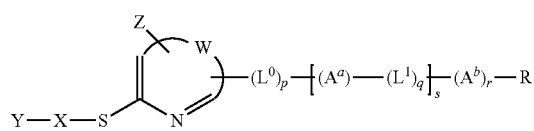

wherein

W, together with other ring member atoms, forms a nitrogen-containing heterocycle selected from the group consisting of a pyridine ring, a pyrazine ring, an imidazole ring, an oxazole ring, a thiazole ring, a quinoline ring, an isoquinoline ring, a quinoxaline ring, a phenanthroline ring, a pteridine ring, and an azocine ring, X is —O— or —NH—, Y is selected from the group consisting of: a substituted or unsubstituted alkyl group selected from the group consisting of methyl, ethyl, n-propyl, isopropyl, n-butyl, isobutyl, sec-butyl, tert-butyl, n-pentyl, isopentyl, neopentyl, 1,2-dimethylpropyl, n-hexyl, 1,3-dimethylbutyl, 1-isopropylpropyl, 1,2-dimethylbutyl, n-heptyl, 1,4-dimethylpentyl, 2-methyl-1-isopropylpropyl, 1-ethyl-3-methylbutyl, n-octyl, 2-ethylhexyl, 3-methyl-1-isopropylbutyl, 2-methyl-1-isopropyl, 1-tert-butyl-2-methylpropyl, n-nonyl, and 3,5,5-trimethylhexyl; a substituted or unsubstituted alkenyl group selected from the group consisting of vinyl, allyl, isopropenyl, 1-butenyl, 2-butenyl, 2-methyl-2-propenyl, 1-methyl-2-propenyl, 2-methyl-1-propenyl, a pentenyl, 1-hexenyl, and 3,3-dimethyl-1-butenyl; a substituted or unsubstituted alkynyl group selected from the group consisting of ethynyl, 1-propynyl, 2-propynyl, 1-butynyl, 2-butynyl, 3-butynyl, 3-methyl-1-propynyl, 2-methyl-3-propynyl, pentynyl, 1-hexynyl, 3-methyl-1-butynyl, and 3,3-dimethyl-1-butynyl; a substituted or unsubstituted cycloalkyl group selected from the group consisting of cyclobutyl, cyclopentyl, cyclohexyl, cycloheptyl, and cyclooctyl; a substituted or unsubstituted cycloalkenyl group selected from the group consisting of cyclobutenyl, cyclopentenyl, and cyclohexenyl; a substituted or unsubstituted aryl group selected from the group consisting of phenyl, 1-naphthyl, 2-naphthyl, 1-anthracenyl, 2-anthracenyl, and 9-anthracenyl; a substituted or unsubstituted heteroaryl group selected from the group consisting of 2-thienyl, 4-pyridyl, 3-pyridyl, 2-pyridyl, 1-pyridyl, 2-furyl, 2-pyrimidinyl, 2-benzothiazolyl, 1-imidazolyl, 1-pyrazolyl, benzotriazol-1-yl, and 7-azabenzotriazol-1-yl; and a a substituted or unsubstituted group selected from the group consisting of phthalimidyl, glutarimidyl, bornane-2,3-dicarboximidyl, morpholinyl, succinimidyl, maleimidyl, 5-norbornene-2,3-dicarboximidyl, 3-hydantoinyl, and piperidinyl;

Z represents a hydrogen atom or an electron-withdrawing substituent selected from the group consisting of nitro, trifluoromethyl, fluorine, chlorine, bromine, iodine, acetyl, methanesulfonyl, trifluoroacetyl, trifluoromethane sulfonyl, and cyano, present on the nitrogen-containing heterocycle, p, q, and r are each independently 0 or 1, s represents an integer of 0 to 10, $L^0$ and $L^1$ each independently represent a linker selected from the group consisting of C1-C6 alkylene, polyoxyalkylene having a molecular weight of 100 to 1000, and linkers represented by Chemical Formula (a),

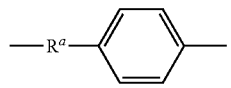

(a)

wherein $R^a$ represents substituted or unsubstituted C1-C8 alkylene;

$A^a$ and $A^b$ are each independently a group selected from the group consisting of —CH=CH—, —C≡C—, —C(=O)—, —C(=O)—O—, —O—C(=O)—, —O—, oxyalkylene group, alkyleneoxy group, —C(=O)—NH—, —NH—C(=O)—, —NH—C(=O)—NH—, hydrazine, triazole, sulfone, sulfoxide, sulfonic acid ester, sulfonamide, sulfinic acid ester, sulfinamide, piperidine, and dioxane, and R is a hydrogen atom, a substituted or unsubstituted alkyl group selected from the group consisting of methyl, ethyl, n-propyl, isopropyl, n-butyl, isobutyl, sec-butyl, tert-butyl, n-pentyl, isopentyl, neopentyl, 1,2-dimethylpropyl, n-hexyl, 1,3-dimethylbutyl, 1-isopropylpropyl, 1,2-dimethylbutyl, n-heptyl, 1,4-dimethylpentyl, 2-methyl-1-isopropylpropyl, 1-ethyl-3-methylbutyl, n-octyl, 2-ethylhexyl, 3-methyl-1-isopropylbutyl, 2-methyl-1-isopropyl, 1-tert-butyl-2-methylpropyl, n-nonyl, and 3,5,5-trimethylhexyl; a substituted or unsubstituted alkenyl group selected from the group consisting of vinyl, allyl, isopropenyl, 1-butenyl, 2-butenyl, 2-methyl-2-propenyl, 1-methyl-2-propenyl, 2-methyl-1-propenyl, pentenyl, 1-hexenyl, and 3,3-dimethyl-1-butenyl; a substituted or unsubstituted alkynyl group selected from the group consisting of ethynyl, 1-propynyl, 2-propynyl, 1-butynyl, 2-butynyl, 3-butynyl, 3-methyl-1-propynyl, 2-methyl-3-propynyl, pentynyl, 1-hexynyl, 3-methyl-1-butynyl, and 3,3-dimethyl-1-butynyl; a substituted or unsubstituted cycloalkyl group selected from the group consisting of cyclobutyl, cyclopentyl, cyclohexyl, cycloheptyl, and cyclooctyl; a substituted or unsubstituted cycloalkenyl group selected from the group consisting of cyclobutenyl, cyclopentenyl, and cyclohexenyl; a substituted or unsubstituted aryl group selected from the group consisting of phenyl, 1-naphthyl, 2-naphthyl, 1-anthracenyl, 2-anthracenyl, and 9-anthracenyl; a substituted or unsubstituted heteroaryl group selected from the group consisting of 2-thienyl, 4-pyridyl, 3-pyridyl, 2-pyridyl, 1-pyridyl, 2-furyl, 2-pyrimidinyl, 2-benzothiazolyl, 1-imidazolyl, 1-pyrazolyl, benzotriazol-1-yl, and 7-azabenzotriazol-1-yl; an amino group a hydroxy group or a polymer carrier;

provided that the following compounds (A) to (H) are excluded:

(A) 3-nitro-2-pyridine sulfinic acid methyl, (B) 3-nitro-2-pyridine sulfinic acid ethyl, (C) 3-nitro-2-pyridine sulfinic acid N,N-diethylaminoethyl, (D) N-(3'-nitro-T-pyridinesulfenyloxy)-5-norbornene-2,3-dicarboximide, (E) (S)-((tert-butoxycarbonyl)amino)-3-(((3-nitropyridin-2-yl)thio)oxy)propanoic acid, (F) (2S,3R)-2-(((benzyloxy)carbonyl)amino)-3-(((3-nitropyridin-2-yl)thio)oxy)butanoic acid, (G) 4-((((3-nitropyridin-2-yl)thio)oxy)methyl)benzoic acid, and (H) (S)-2-(((3-nitropyridin-2-yl)thio)oxy)-3-phenylpropanoic acid.

2. The nitrogen-containing compound or a salt thereof according to claim 1, wherein the nitrogen-containing compound or the salt thereof does not satisfy the following conditions:

Conditions: p=0, s=0, r=0, and R=hydrogen atom.

3. The nitrogen-containing compound or a salt thereof according to claim 1, wherein W, together with other ring member atoms, forms a pyridine ring as the nitrogen-containing heterocycle.

4. The nitrogen-containing compound or a salt thereof according to claim 1, wherein X is —O—.

5. The nitrogen-containing compound or a salt thereof according to claim 1, wherein Y is a substituted or unsubstituted alkyl group selected from the group consisting of methyl, ethyl, n-propyl, isopropyl, n-butyl, isobutyl, sec-butyl, tert-butyl, n-pentyl, isopentyl, neopentyl, 1,2-dimethylpropyl, n-hexyl, 1,3-dimethylbutyl, 1-isopropylpropyl, 1,2-dimethylbutyl, n-heptyl, 1,4-dimethylpentyl, 2-methyl-1-isopropylpropyl, 1-ethyl-3-methylbutyl, n-octyl, 2-ethylhexyl, 3-methyl-1-isopropylbutyl, 2-methyl-1-isopropyl, 1-tert-butyl-2-methylpropyl, n-nonyl, and 3,5,5-trimethylhexyl; or a substituted or unsubstituted aryl group selected from the group consisting of phenyl, 1-naphthyl, 2-naphthyl, 1-anthracenyl, 2-anthracenyl, and 9-anthracenyl.

6. The nitrogen-containing compound or a salt thereof according to claim 5, wherein Y is a substituted or unsubstituted alkyl group selected from the group consisting of methyl, ethyl, n-propyl, isopropyl, n-butyl, isobutyl, sec-butyl, tert-butyl, n-pentyl, isopentyl, neopentyl, 1,2-dimethylpropyl, n-hexyl, 1,3-dimethylbutyl, 1-isopropylpropyl, 1,2-dimethylbutyl, n-heptyl, 1,4-dimethylpentyl, 2-methyl-1-isopropylpropyl, 1-ethyl-3-methylbutyl, n-octyl, 2-ethylhexyl, 3-methyl-1-isopropylbutyl, 2-methyl-1-isopropyl, 1-tert-butyl-2-methylpropyl, n-nonyl, and 3,5,5-trimethylhexyl.

7. The nitrogen-containing compound or a salt thereof according to claim 1, wherein Z is an electron-withdrawing substituent selected from the group consisting of nitro, trifluoromethyl, fluorine, chlorine, bromine, iodine, acetyl, methanesulfonyl, trifluoroacetyl, trifluoromethane sulfonyl, and cyano.

8. The nitrogen-containing compound or a salt thereof according to claim 7, wherein the electron-withdrawing substituent is selected from the group consisting of nitro, trifluoromethyl, fluorine, chlorine, bromine and iodine.

9. The nitrogen-containing compound or a salt thereof according to claim 1, wherein the nitrogen-containing compound is represented by Chemical Formula 2 below:

Chemical Formula 2

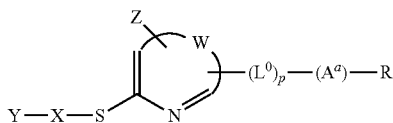

wherein

W, X, Y, Z, p, $L^o$, and $A^a$ are the same as defined in claim 1, and

R is a hydrogen atom, a substituted or unsubstituted alkyl group selected from the group consisting of methyl, ethyl, n-propyl, isopropyl, n-butyl, isobutyl, sec-butyl, tert-butyl, n-pentyl, isopentyl, neopentyl, 1,2-dimethylpropyl, n-hexyl, 1,3-dimethylbutyl, 1-isopropylpropyl, 1,2-dimethylbutyl, n-heptyl, 1,4-dimethylpentyl, 2-methyl-1-isopropylpropyl, 1-ethyl-3-methylbutyl, n-octyl, 2-ethylhexyl, 3-methyl-1-isopropylbutyl, 2-methyl-1-isopropyl, 1-tert-butyl-2-methylpropyl, n-nonyl, and 3,5,5-trimethylhexyl; a substituted or unsubstituted alkenyl group selected from the group consisting of vinyl, allyl, isopropenyl, 1-butenyl, 2-butenyl, 2-methyl-2-propenyl, 1-methyl-2-propenyl, 2-methyl-1-propenyl, pentenyl, 1-hexenyl, and 3,3-dimethyl-1-butenyl; a substituted or unsubstituted alkynyl group selected from the group consisting of ethynyl, 1-propynyl, 2-propynyl, 1-butynyl, 2-butynyl, 3-butynyl, 3-methyl-1-propynyl, 2-methyl-3-propynyl, pentynyl, 1-hexynyl, 3-methyl-1-butynyl, and 3,3-dimethyl-1-butynyl; a substituted or unsubstituted cycloalkyl group selected from the group consisting of cyclobutyl, cyclopentyl, cyclohexyl, cycloheptyl, and cyclooctyl; a substituted or unsubstituted cycloalkenyl group selected from the group consisting of cyclobutenyl, cyclopentenyl, and cyclohexenyl; a substituted or unsubstituted aryl group selected from the group consisting of phenyl, 1-naphthyl, 2-naphthyl, 1-anthracenyl, 2-anthracenyl, and 9-anthracenyl; or a substituted or unsubstituted heteroaryl group selected from the group consisting of 2-thienyl, 4-pyridyl, 3-pyridyl, 2-pyridyl, 1-pyridyl, 2-furyl, 2-pyrimidinyl, 2-benzothiazolyl, 1-imidazolyl, 1-pyrazolyl, benzotriazol-1-yl, and 7-azabenzotriazol-1-yl.

10. The nitrogen-containing compound or a salt thereof according to claim 9, wherein R is a substituted or unsubstituted alkyl group selected from the group consisting of methyl, ethyl, n-propyl, isopropyl, n-butyl, isobutyl, sec-butyl, tert-butyl, n-pentyl, isopentyl, neopentyl, 1,2-dimethylpropyl, n-hexyl, 1,3-dimethylbutyl, 1-isopropylpropyl, 1,2-dimethylbutyl, n-heptyl, 1,4-dimethylpentyl, 2-methyl-1-isopropylpropyl, 1-ethyl-3-methylbutyl, n-octyl, 2-ethylhexyl, 3-methyl-1-isopropylbutyl, 2-methyl-1-isopropyl, 1-tert-butyl-2-methylpropyl, n-nonyl, and 3,5,5-trimethylhexyl.

11. The nitrogen-containing compound or a salt thereof according to claim 9, wherein $A^a$ is selected from the group consisting of —C(=O)—, —C(=O)—O—, —O—C(=O)—, —O—, —C(=O)—NH—, and —NH—C(=O)—.

12. The nitrogen-containing compound or a salt thereof according to claim 11, wherein $A^a$ is —C(=O)—O—.

13. The nitrogen-containing compound or a salt thereof according to claim 9, wherein p is 0.

14. The nitrogen-containing compound or a salt thereof according to claim 1, wherein R is a polymer carrier.

15. The nitrogen-containing compound or a salt thereof according to claim 14, wherein R is a polymer carrier used in a solid phase synthesis method.

16. The nitrogen-containing compound or a salt thereof according to claim 14, wherein R is selected from the group consisting of polystyrene, polypropylene, polyethylene, polyether, polyvinyl chloride, dextran, polyacrylamide, polyethylene glycol, copolymers and crosslinked products thereof, magnetic beads, and a combination thereof.

17. The nitrogen-containing compound or a salt thereof according to claim 14, wherein the nitrogen-containing compound is represented by Chemical Formula 3 below:

Chemical Formula 3

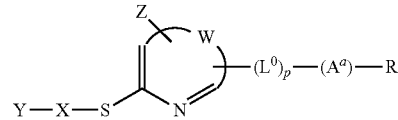

wherein W, X, Y, Z, p, $L^o$, and $A^a$ are the same as defined in claim 1, and R is a polymer carrier.

18. The nitrogen-containing compound or a salt thereof according to claim 17, wherein $A^a$ is selected from the group consisting of —C(=O)—, —C(=O)—O—, —O—C(=O)—, —O—, —C(=O)—NH—, and —NH—C(=O)—.

19. The nitrogen-containing compound or a salt thereof according to claim 18, wherein $A^a$ is —C(=O)—NH—, and R is a polyethylene glycol crosslinked product.

20. The nitrogen-containing compound or a salt thereof according to claim 18, wherein $A^a$ is —C(=O)—O—, and R is a polystyrene resin.

21. The nitrogen-containing compound or a salt thereof according to claim 14, wherein p is 0.

22. The nitrogen-containing compound or a salt thereof according to claim 14, wherein the nitrogen-containing compound is represented by Chemical Formula 4 below:

Chemical Formula 4

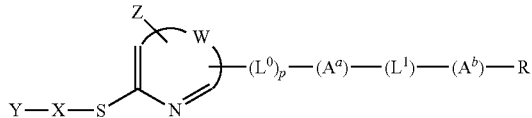

wherein W, X, Y, Z, p, $L^0$, $L^1$, $A^a$, and $A^b$ are the same as defined in claim 1, and R is a polymer carrier.

23. The nitrogen-containing compound or a salt thereof according to claim 22, wherein $A^a$ and $A^b$ are —C(=O)—NH—, $L^1$ is a C1-C6 alkylene group, and R is a polyethylene glycol crosslinked product.

24. The nitrogen-containing compound or a salt thereof according to claim 22, wherein p is 0.

25. A method for producing the nitrogen-containing compound or a salt thereof according to claim 1, the method comprising:
(I) reacting a compound represented by Chemical Formula 5 below with a halogen simple substance or a halogen generating reagent to produce a compound represented by Chemical Formula 6 below;

Chemical Formula 5

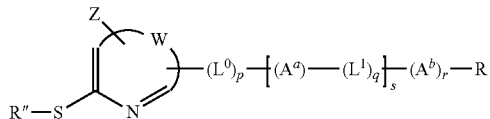

wherein W, Z, p, q, r, s, $L^0$, $L^1$, $A^a$, and $A^b$ are the same as defined in claim 1, and R'' is a leaving group, Chemical Formula 6

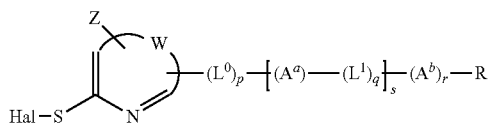

wherein W, Z, p, q, r, s, $L^0$, $L^1$, $A^a$, and $A^b$ are the same as defined in claim 1, and Hal represents a halogen atom selected from fluorine, chlorine, bromine or iodine, and
(II) reacting the compound represented by Chemical Formula 6 with an alcohol represented by Y—OH or an amine represented by Y—NH$_2$ under basic conditions, wherein Y is the same as defined in Chemical Formula 1, thereby producing a nitrogen-containing compound represented by Chemical Formula 1 below:

Chemical Formula 1

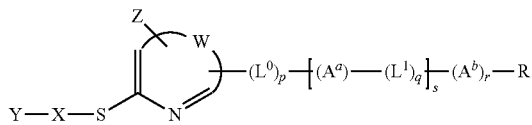

wherein W, X, Y, Z, p, q, r, s, $L^0$, $L^1$, $A^a$, and $A^b$ are the same as defined in claim 1.

26. The nitrogen-containing compound or a salt thereof according to claim 1, wherein: Y is selected from the group consisting of a substituted or unsubstituted alkyl group selected from the group consisting of methyl, ethyl, n-propyl, isopropyl, n-butyl, isobutyl, sec-butyl, tert-butyl, n-pentyl, isopentyl, neopentyl, a 1,2-dimethylpropyl, n-hexyl, 1,3-dimethylbutyl, 1-isopropylpropyl, and 1,2-dimethylbutyl group; a substituted or unsubstituted alkenyl group selected from the group consisting of vinyl, allyl, isopropenyl, 1-butenyl, 2-butenyl, 2-methyl-2-propenyl, 1-methyl-2-propenyl, and 2-methyl-1-propenyl; a substituted or unsubstituted alkynyl group selected from the group consisting of ethynyl, 1-propynyl, 2-propynyl, 1-butynyl, 2-butynyl, 3-butynyl, 3-methyl-1-propynyl, and 2-methyl-3-propynyl; a substituted or unsubstituted cycloalkyl group selected from the group consisting of cyclobutyl, cyclopentyl, and cyclohexyl; a substituted or unsubstituted cycloalkenyl group selected from the group consisting of cyclobutenyl, cyclopentenyl, and cyclohexenyl; a substituted or unsubstituted aryl group selected from the group consisting of phenyl, 1-naphthyl group, and 2-naphthyl; a substituted or unsubstituted heteroaryl group selected from the group consisting of 2-thienyl, 4-pyridyl, 3-pyridyl, 2-pyridyl, 1-pyridyl, 2-furyl, 2-pyrimidinyl, 2-benzothiazolyl, 1-imidazolyl, 1-pyrazolyl, benzotriazol-1-yl, and 7-azabenzotriazol-1-yl; and a substituted or unsubstituted group selected from the group consisting of phthalimidyl, glutarimidyl, bornane-2,3-dicarboximidyl, morpholinyl, succinimidyl, maleimidyl, 5-norbornene-2,3-dicarboximidyl, 3-hydantoinyl, and piperidinyl group;
Z represents a hydrogen atom or an electron-withdrawing substituent selected from the group consisting of nitro, trifluoromethyl, fluorine, chlorine, bromine, iodine, acetyl, methanesulfonyl, trifluoroacetyl, trifluoromethane sulfonyl, and cyano, present on the nitrogen-containing heterocycle;
$L^0$ and $L^1$ each independently represent a linker selected from the group consisting of C1-C6 alkylene and a group represented by the Chemical Formula (a), (a)

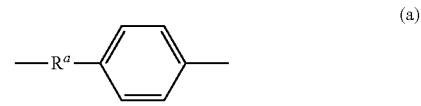

wherein $R^a$ represents a substituted or unsubstituted C1-C8 alkylene;
R is a hydrogen atom, a substituted or unsubstituted alkyl group selected from the group consisting of methyl, ethyl, n-propyl, isopropyl, n-butyl, isobutyl, sec-butyl, tert-butyl, n-pentyl, isopentyl, neopentyl, 1,2-dimethylpropyl, n-hexyl, 1,3-dimethylbutyl, 1-isopropylpropyl, and 1,2-dimethylbutyl; a substituted or unsubstituted alkenyl group selected from the group consisting of vinyl, allyl, isopropenyl, 1-butenyl, 2-butenyl, 2-methyl-2-propenyl, 1-methyl-2-propenyl, and 2-methyl-1-propenyl; a substituted or unsubstituted alkynyl group selected from the group consisting of ethynyl, 1-propynyl, 2-propynyl, 1-butynyl, 2-butynyl, 3-butynyl, 3-methyl-1-propynyl, and 2-methyl-3-propynyl; a substituted or unsubstituted cycloalkyl group selected from the group consisting of cyclobutyl, cyclopentyl, and cyclohexyl; a substituted or unsubstituted cycloalkenyl group selected from the group consisting of cyclobutenyl, cyclopentenyl, and cyclohexenyl; a substituted or unsubstituted aryl group selected from the group consisting of phenyl, 1-naphthyl, and 2-naphthyl; a substituted or unsubstituted heteroaryl group selected from the group consisting of 2-thienyl, 4-pyridyl, 3-pyridyl, 2-pyridyl, 1-pyridyl, 2-furyl, 2-pyrimidinyl, 2-benzothiazolyl, 1-imidazolyl, 1-pyrazolyl, benzotriazol-1-yl, and 7-azabenzotriazol-1-yl group; an amino group; a hydroxy group; or a polymer carrier.

27. The nitrogen-containing compound or a salt thereof according to claim 1, wherein: Y is selected from the group consisting of a substituted or unsubstituted alkyl group selected from the group consisting of methyl, ethyl, n-propyl, isopropyl, n-butyl, isobutyl, sec-butyl, tert-butyl, n-pentyl, isopentyl, neopentyl, 1,2-dimethylpropyl, n-hexyl, 1,3-dimethylbutyl, 1-isopropylpropyl, and 1,2-dimethylbutyl group; a substituted or unsubstituted alkenyl group selected from the group consisting of vinyl, allyl, isopropenyl, 1-butenyl, 2-butenyl, 2-methyl-2-propenyl, 1-methyl-2-propenyl, and 2-methyl-1-propenyl; a substituted or unsubstituted alkynyl group selected from the group consisting of ethynyl, 1-propynyl, 2-propynyl, 1-butynyl, 2-butynyl, 3-butynyl, 3-methyl-1-propynyl, and 2-methyl-3-propynyl; a substituted or unsubstituted cycloalkyl group selected from the group consisting of cyclobutyl, cyclopentyl, and cyclohexyl; a substituted or unsubstituted cycloalkenyl group selected from the group consisting of cyclobutenyl, cyclopentenyl, and cyclohexenyl; a substituted or unsubstituted aryl group selected from the group consisting of phenyl, 1-naphthyl, and 2-naphthyl; a substituted or unsubstituted heteroaryl group selected from the group consisting of 2-thienyl, 4-pyridyl, 3-pyridyl, 2-pyridyl, 1-pyridyl, 2-furyl, 2-pyrimidinyl, 2-benzothiazolyl, 1-imidazolyl, 1-pyrazolyl, benzotriazol-1-yl, and 7-azabenzotriazol-1-yl; and a substituted or unsubstituted group selected from the group consisting of phthalimidyl, glutarimidyl, bornane-2,3-dicarboximidyl, morpholinyl, succinimidyl, maleimidyl, a 5-norbornene-2,3-dicarboximidyl, 3-hydantoinyl, and piperidinyl;

Z represents a hydrogen atom or an electron-withdrawing substituent selected from the group consisting of nitro, trifluoromethyl, fluorine, chlorine, bromine, iodine, acetyl group, methanesulfonyl, trifluoroacetyl, trifluoromethane sulfonyl, and cyano, present on the nitrogen-containing heterocycle;

$L^0$ and $L^1$ each independently represent a linker selected from the group consisting of C1-C6 alkylene group and a group represented by the Chemical Formula (a),

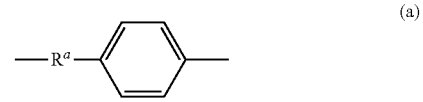

(a)

wherein $R^a$ represents substituted or unsubstituted C1-C8 alkylene;

R is hydrogen; a substituted or unsubstituted alkyl group selected from the group consisting of methyl, ethyl, n-propyl, isopropyl, n-butyl, isobutyl, sec-butyl, tert-butyl, n-pentyl, isopentyl, neopentyl, 1,2-dimethylpropyl, n-hexyl, 1,3-dimethylbutyl, 1-isopropylpropyl, and 1,2-dimethylbutyl group; a substituted or unsubstituted alkenyl group selected from the group consisting of vinyl, allyl, isopropenyl, 1-butenyl, 2-butenyl, 2-methyl-2-propenyl, 1-methyl-2-propenyl, and 2-methyl-1-propenyl; a substituted or unsubstituted alkynyl group selected from the group consisting of ethynyl, 1-propynyl, 2-propynyl, 1-butynyl, 2-butynyl, 3-butynyl, 3-methyl-1-propynyl, and 2-methyl-3-propynyl; a substituted or unsubstituted cycloalkyl group selected from the group consisting of cyclobutyl, cyclopentyl, and cyclohexyl; a substituted or unsubstituted cycloalkenyl group selected from the group consisting of cyclobutenyl, cyclopentenyl, and cyclohexenyl; a substituted or unsubstituted aryl group selected from the group consisting of phenyl group, 1-naphthyl, and 2-naphthyl; a substituted or unsubstituted heteroaryl group selected from the group consisting of 2-thienyl, 4-pyridyl, 3-pyridyl, 2-pyridyl, 1-pyridyl, 2-furyl, 2-pyrimidinyl, 2-benzothiazolyl, 1-imidazolyl, 1-pyrazolyl, benzotriazol-1-yl, and 7-azabenzotriazol-1-yl; an amino group; a hydroxy group; or a polymer carrier.

* * * * *

SEQUENCE LISTING

```
<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: Syntheseized Oxytocin precursor bound to solid
      phase
<220> FEATURE:
<221> NAME/KEY: BINDING
<222> LOCATION: (1)..(1)
```

```
<223> OTHER INFORMATION: Cysteine substituted with trityl (Trt) group
<220> FEATURE:
<221> NAME/KEY: BINDING
<222> LOCATION: (2)..(2)
<223> OTHER INFORMATION: Tyrosine substituted with tert-butyl (t-Bu)
      group
<220> FEATURE:
<221> NAME/KEY: BINDING
<222> LOCATION: (4)..(4)
<223> OTHER INFORMATION: Glutamine substituted with trityl (Trt) group
<220> FEATURE:
<221> NAME/KEY: BINDING
<222> LOCATION: (5)..(5)
<223> OTHER INFORMATION: Asparagine substituted with trityl (Trt) group
<220> FEATURE:
<221> NAME/KEY: BINDING
<222> LOCATION: (6)..(6)
<223> OTHER INFORMATION: Cysteine substituted with trityl (Trt) group
<220> FEATURE:
<221> NAME/KEY: BINDING
<222> LOCATION: (9)..(9)
<223> OTHER INFORMATION: Glycine bound to solid phase

<400> SEQUENCE: 1

Xaa Xaa Ile Xaa Xaa Xaa Pro Leu Xaa
1               5

<210> SEQ ID NO 2
<211> LENGTH: 9
<212> TYPE: PRT
<213> ORGANISM: Artificial Sequence
<220> FEATURE:
<223> OTHER INFORMATION: Oxytocin without disulfide crosslink

<400> SEQUENCE: 2

Cys Tyr Ile Gln Asn Cys Pro Leu Gly
1               5

<210> SEQ ID NO 3
<211> LENGTH: 9
<212> TYPE: PRT
<213> ORGANISM: Artificial Sequence
<220> FEATURE:
<223> OTHER INFORMATION: Oxytocin with a disulfide crosslink
<220> FEATURE:
<221> NAME/KEY: DISULFID
<222> LOCATION: (1)..(6)

<400> SEQUENCE: 3

Cys Tyr Ile Gln Asn Cys Pro Leu Gly
1               5

<210> SEQ ID NO 4
<211> LENGTH: 28
<212> TYPE: PRT
<213> ORGANISM: Artificial Sequence
<220> FEATURE:
<223> OTHER INFORMATION: Syntheseized human Atrial Natriuretic Peptide
      precursor bound to solid phase
<220> FEATURE:
<221> NAME/KEY: BINDING
<222> LOCATION: (1)..(1)
<223> OTHER INFORMATION: Serine substituted with tert-butyl (t-Bu) group
<220> FEATURE:
<221> NAME/KEY: BINDING
<222> LOCATION: (3)..(3)
<223> OTHER INFORMATION: Arginine substituted with
      2,2,4,6,7-pentamethyldihydrobenzofuran-5-sulfonyl (Pbf) group
<220> FEATURE:
<221> NAME/KEY: BINDING
<222> LOCATION: (4)..(4)
<223> OTHER INFORMATION: Arginine substituted with
      2,2,4,6,7-pentamethyldihydrobenzofuran-5-sulfonyl (Pbf) group
```

```
<220> FEATURE:
<221> NAME/KEY: BINDING
<222> LOCATION: (5)..(5)
<223> OTHER INFORMATION: Serine substituted with tert-butyl (t-Bu) group
<220> FEATURE:
<221> NAME/KEY: BINDING
<222> LOCATION: (6)..(6)
<223> OTHER INFORMATION: Serine substituted with tert-butyl (t-Bu) group
<220> FEATURE:
<221> NAME/KEY: BINDING
<222> LOCATION: (7)..(7)
<223> OTHER INFORMATION: Cysteine substituted with trityl (Trt) group
<220> FEATURE:
<221> NAME/KEY: BINDING
<222> LOCATION: (11)..(11)
<223> OTHER INFORMATION: Arginine substituted with
      2,2,4,6,7-pentamethyldihydrobenzofuran-5-sulfonyl (Pbf) group
<220> FEATURE:
<221> NAME/KEY: BINDING
<222> LOCATION: (13)..(13)
<223> OTHER INFORMATION: Aspartic acid substituted with tert-butoxy
      (Ot-Bu) group
<220> FEATURE:
<221> NAME/KEY: BINDING
<222> LOCATION: (14)..(14)
<223> OTHER INFORMATION: Arginine substituted with
      2,2,4,6,7-pentamethyldihydrobenzofuran-5-sulfonyl (Pbf) group
<220> FEATURE:
<221> NAME/KEY: BINDING
<222> LOCATION: (18)..(18)
<223> OTHER INFORMATION: Glutamine substituted with trityl (Trt) group
<220> FEATURE:
<221> NAME/KEY: BINDING
<222> LOCATION: (19)..(19)
<223> OTHER INFORMATION: Serine substituted with tert-butyl (t-Bu) group
<220> FEATURE:
<221> NAME/KEY: BINDING
<222> LOCATION: (23)..(23)
<223> OTHER INFORMATION: Cysteine substituted with trityl (Trt) group
<220> FEATURE:
<221> NAME/KEY: BINDING
<222> LOCATION: (24)..(24)
<223> OTHER INFORMATION: Asparagine substituted with trityl (Trt) group
<220> FEATURE:
<221> NAME/KEY: BINDING
<222> LOCATION: (25)..(25)
<223> OTHER INFORMATION: Serine substituted with tert-butyl (t-Bu) group
<220> FEATURE:
<221> NAME/KEY: BINDING
<222> LOCATION: (27)..(27)
<223> OTHER INFORMATION: Arginine substituted with
      2,2,4,6,7-pentamethyldihydrobenzofuran-5-sulfonyl (Pbf) group
<220> FEATURE:
<221> NAME/KEY: BINDING
<222> LOCATION: (28)..(28)
<223> OTHER INFORMATION: Tyrosine substituted with tert-butyl (t-Bu)
      group and bound to solid phase

<400> SEQUENCE: 4

Xaa Leu Xaa Xaa Xaa Xaa Xaa Phe Gly Gly Xaa Met Xaa Xaa Ile Gly
1               5                   10                  15

Ala Xaa Xaa Gly Leu Gly Xaa Xaa Xaa Phe Xaa Xaa
            20                  25

<210> SEQ ID NO 5
<211> LENGTH: 28
<212> TYPE: PRT
<213> ORGANISM: Artificial Sequence
<220> FEATURE:
<223> OTHER INFORMATION: human Atrial Natriuretic Peptide without
      difulfide crosslink

<400> SEQUENCE: 5

Ser Leu Arg Arg Ser Ser Cys Phe Gly Gly Arg Met Asp Arg Ile Gly
1               5                   10                  15
```

```
Ala Gln Ser Gly Leu Gly Cys Asn Ser Phe Arg Tyr
            20                  25

<210> SEQ ID NO 6
<211> LENGTH: 28
<212> TYPE: PRT
<213> ORGANISM: Artificial Sequence
<220> FEATURE:
<223> OTHER INFORMATION: human Atrial Natriuretic Peptide with a
      disulfide crosslink
<220> FEATURE:
<221> NAME/KEY: DISULFID
<222> LOCATION: (7)..(23)

<400> SEQUENCE: 6

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 7
<211> LENGTH: 12
<212> TYPE: PRT
<213> ORGANISM: Artificial Sequence
<220> FEATURE:
<223> OTHER INFORMATION: Syntheseized alpha-conotoxin ImI precursor
      bound to solid phase
<220> FEATURE:
<221> NAME/KEY: BINDING
<222> LOCATION: (2)..(2)
<223> OTHER INFORMATION: Cysteine substituted with trityl (Trt) group
<220> FEATURE:
<221> NAME/KEY: BINDING
<222> LOCATION: (3)..(3)
<223> OTHER INFORMATION: Cysteine substituted with acetamidemethyl
      (Acm) group
<220> FEATURE:
<221> NAME/KEY: BINDING
<222> LOCATION: (4)..(4)
<223> OTHER INFORMATION: Serine substituted with tert-butyl (t-Bu) group
<220> FEATURE:
<221> NAME/KEY: BINDING
<222> LOCATION: (5)..(5)
<223> OTHER INFORMATION: Aspartic acid substituted with tert-butyl
      (t-Bu) group
<220> FEATURE:
<221> NAME/KEY: BINDING
<222> LOCATION: (7)..(7)
<223> OTHER INFORMATION: Arginine substituted with
      2,2,4,6,7-pentamethyldihydrobenzofuran-5-sulfonyl (Pbf) group
<220> FEATURE:
<221> NAME/KEY: BINDING
<222> LOCATION: (8)..(8)
<223> OTHER INFORMATION: Cysteine substituted with trityl (Trt) group
<220> FEATURE:
<221> NAME/KEY: BINDING
<222> LOCATION: (10)..(10)
<223> OTHER INFORMATION: Tryptophan substituted with tert-butoxycarbonyl
      (Boc) group
<220> FEATURE:
<221> NAME/KEY: BINDING
<222> LOCATION: (11)..(11)
<223> OTHER INFORMATION: Arginine substituted with
      2,2,4,6,7-pentamethyldihydrobenzofuran-5-sulfonyl (Pbf) group
<220> FEATURE:
<221> NAME/KEY: BINDING
<222> LOCATION: (12)..(12)
<223> OTHER INFORMATION: Cysteine substituted with acetamidemethyl (Acm)
      group and bound to solid phase

<400> SEQUENCE: 7

Gly Xaa Xaa Xaa Xaa Pro Xaa Xaa Ala Xaa Xaa Xaa
1               5                   10
```

<210> SEQ ID NO 8
<211> LENGTH: 12
<212> TYPE: PRT
<213> ORGANISM: Artificial Sequence
<220> FEATURE:
<223> OTHER INFORMATION: alpha-Conotoxin ImI without disulfide crosslink
<220> FEATURE:
<221> NAME/KEY: BINDING
<222> LOCATION: (3)..(3)
<223> OTHER INFORMATION: Cysteine substituted with acetamidemethyl (Acm)
      group
<220> FEATURE:
<221> NAME/KEY: BINDING
<222> LOCATION: (12)..(12)
<223> OTHER INFORMATION: Cysteine substituted with acetamidemethyl (Acm)
      group

<400> SEQUENCE: 8

Gly Cys Xaa Ser Asp Pro Arg Cys Ala Trp Arg Xaa
1               5                   10

<210> SEQ ID NO 9
<211> LENGTH: 12
<212> TYPE: PRT
<213> ORGANISM: Artificial Sequence
<220> FEATURE:
<223> OTHER INFORMATION: alpha-Conotoxin ImI with a disulfide crosslink
<220> FEATURE:
<221> NAME/KEY: DISULFID
<222> LOCATION: (2)..(8)
<220> FEATURE:
<221> NAME/KEY: BINDING
<222> LOCATION: (3)..(3)
<223> OTHER INFORMATION: Cysteine substituted with acetamidemethyl (Acm)
      group
<220> FEATURE:
<221> NAME/KEY: BINDING
<222> LOCATION: (12)..(12)
<223> OTHER INFORMATION: Cysteine substituted with acetamidemethyl (Acm)
      group

<400> SEQUENCE: 9

Gly Cys Xaa Ser Asp Pro Arg Cys Ala Trp Arg Xaa
1               5                   10

<210> SEQ ID NO 10
<211> LENGTH: 12
<212> TYPE: PRT
<213> ORGANISM: Artificial Sequence
<220> FEATURE:
<223> OTHER INFORMATION: alpha-Conotoxin ImI with two disulfide
      crosslinks
<220> FEATURE:
<221> NAME/KEY: DISULFID
<222> LOCATION: (2)..(8)
<220> FEATURE:
<221> NAME/KEY: DISULFID
<222> LOCATION: (3)..(12)

<400> SEQUENCE: 10

Gly Cys Cys Ser Asp Pro Arg Cys Ala Trp Arg Cys
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Syntheseized Oxytocin precursor bound to solid
      phase
<220> FEATURE:

```
<221> NAME/KEY: BINDING
<222> LOCATION: (1)..(1)
<223> OTHER INFORMATION: Cysteine substituted with t-butylthio (St-Bu)
      group
<220> FEATURE:
<221> NAME/KEY: BINDING
<222> LOCATION: (2)..(2)
<223> OTHER INFORMATION: Tyrosine substituted with tert-butyl (t-Bu)
      group
<220> FEATURE:
<221> NAME/KEY: BINDING
<222> LOCATION: (4)..(4)
<223> OTHER INFORMATION: Glutamine substituted with trityl (Trt) group
<220> FEATURE:
<221> NAME/KEY: BINDING
<222> LOCATION: (5)..(5)
<223> OTHER INFORMATION: Asparagine substituted with trityl (Trt) group
<220> FEATURE:
<221> NAME/KEY: BINDING
<222> LOCATION: (6)..(6)
<223> OTHER INFORMATION: Cysteine substituted with t-butylthio (St-Bu)
      group
<220> FEATURE:
<221> NAME/KEY: BINDING
<222> LOCATION: (9)..(9)
<223> OTHER INFORMATION: Glycine bound to solid phase

<400> SEQUENCE: 11

Xaa Xaa Ile Xaa Xaa Xaa Pro Leu Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: Syntheseized Oxytocin precursor bound to solid
      phase
<220> FEATURE:
<221> NAME/KEY: BINDING
<222> LOCATION: (2)..(2)
<223> OTHER INFORMATION: Tyrosine substituted with tert-butyl (t-Bu)
      group
<220> FEATURE:
<221> NAME/KEY: BINDING
<222> LOCATION: (4)..(4)
<223> OTHER INFORMATION: Glutamine substituted with trityl (Trt) group
<220> FEATURE:
<221> NAME/KEY: BINDING
<222> LOCATION: (5)..(5)
<223> OTHER INFORMATION: Asparagine substituted with trityl (Trt) group
<220> FEATURE:
<221> NAME/KEY: BINDING
<222> LOCATION: (9)..(9)
<223> OTHER INFORMATION: Glycine bound to solid phase

<400> SEQUENCE: 12

Cys Xaa Ile Xaa Xaa Cys Pro Leu Xaa
1               5
```